(12) United States Patent
Hardy et al.

(10) Patent No.: US 8,045,170 B2
(45) Date of Patent: Oct. 25, 2011

(54) LIGHT SCATTERING PROPERTY MEASUREMENT METHOD

(75) Inventors: Stephen James Hardy, West Pymble (AU); DeQiang Eugene Cai, Brighton-Le-Sands (AU)

(73) Assignee: Canon Kabushiki Kaisha, Tokyo (JP)

( * ) Notice: Subject to any disclaimer, the term of this patent is extended or adjusted under 35 U.S.C. 154(b) by 533 days.

(21) Appl. No.: 12/326,783

(22) Filed: Dec. 2, 2008

(65) Prior Publication Data

US 2009/0148175 A1    Jun. 11, 2009

(30) Foreign Application Priority Data

Dec. 5, 2007    (AU) ................................ 2007237364
Dec. 20, 2007   (AU) ................................ 2007254594

(51) Int. Cl.
 *G01N 21/55*   (2006.01)
(52) U.S. Cl. ...................................... 356/445; 356/446
(58) Field of Classification Search .......... 356/445–448, 356/399–401
 See application file for complete search history.

(56) References Cited

U.S. PATENT DOCUMENTS

| | | | |
|---|---|---|---|
| 7,440,105 B2* | 10/2008 | Adel et al. | 356/401 |
| 2003/0224261 A1* | 12/2003 | Schulz | 430/22 |
| 2004/0257571 A1* | 12/2004 | Mieher et al. | 356/401 |
| 2006/0033921 A1* | 2/2006 | Den Boef et al. | 356/446 |
| 2006/0066855 A1* | 3/2006 | Boef et al. | 356/401 |

OTHER PUBLICATIONS

Information Technology—Office Equipment—Measurement of Image Quality Attributes for Hardcopy Output—Binary Monochrome Text and Graphic Images, 2001, pp. 1 to 28.

* cited by examiner

*Primary Examiner* — Hoa Pham
(74) *Attorney, Agent, or Firm* — Fitzpatrick, Cella, Harper & Scinto

(57) ABSTRACT

Methods (300, 1000) of determining a light scattering property of a medium (152), are disclosed. The medium (152) is illuminated through a test pattern (e.g., 155, 510), the test pattern (155, 510) comprising at least one region containing a first pattern with substantial variation in two orthogonal directions at one scale. The test pattern (300, 1000) further comprises at least one other region containing the first pattern at a different scale. The light reflected from the illuminated medium (152) through the test pattern is measured to capture an image of the illuminated medium. A light scattering property of the medium (152) is determined based on the measured light.

22 Claims, 16 Drawing Sheets

LIGHT SCATTERING PROPERTY MEASUREMENT METHOD

CROSS-REFERENCE TO RELATED PATENT APPLICATIONS

This application claims the right of priority under 35 U.S.C. §119 based on Australian Patent Application No. 2007237364, filed 5 Dec. 2007, and based on Australian Patent Application No. 2007254594, filed 20 Dec. 2007, which are both incorporated by reference herein in their entirety as if fully set forth herein.

FIELD OF INVENTION

The current invention relates to measurement of an optical propagation property of a medium and, in particular, to a method and apparatus for determining a light scattering property of a medium and to the determination of the resolution of a printing system compensating for this light scattering property. The present invention also relates to a computer program product including a computer readable medium having recorded thereon a computer program for determining a light scattering property of a medium.

DESCRIPTION OF BACKGROUND ART

Printed matter is ubiquitous in modern society. There are manifold methods of producing printed documents, ranging from large-scale offset printers to small scale personal inkjet printers. Each printed document, regardless of printing mechanism, shares the characteristic that light reflected from that document depends on properties of a medium on which the document has been printed. That is, both colour and reproduction quality of the document depends sensitively on surface properties of the medium, such as bulk physical and chemical properties of the medium. The colour and reproduction quality of the document also depends on optical properties of the medium.

In terms of effect of the optical properties of the medium, light that falls on the document and is reflected towards a user can have taken many paths. In the instance that the medium is paper, some of the light will have been directly reflected off the surface of the paper, and some will have entered the paper and been scattered once or many times. Some of the light will have entered the paper and been reflected off the back surface of the paper. Other light will be absorbed, either by the ink or toner that has been printed on the paper, or by the paper itself.

The diversity of different optical paths within the paper leads to an effect known as optical dot gain (ODG). Optical dot gain may be understood by considering a single line of black toner printed onto the surface of a page. Light that falls onto the toner is mostly absorbed, so the toner itself appears black. Light that falls on the paper surface that is directly next to the edge of the line will ether be reflected off the surface directly, or will enter the bulk of the paper and be scattered there. If the light enters the bulk of the paper, the light has a roughly 50% chance of being scattered under the line of toner, there to be absorbed. This means that only 50% of the light that enters the paper at the edge of the line can escape. For a point further away from the line of toner, a much smaller portion will scatter under the line of toner. This means that areas further from the line of toner will appear brighter than the areas closer to the toner.

In this way, if a dense set of lines is printed on a page that covers exactly 50% of the page, then far less than 50% of the incident illumination will be reflected from the page. Light that falls on the lines will be absorbed, and light that falls between the lines has some probability of entering the paper and scattering under the lines to be absorbed. The actual fraction of the light that scatters and is absorbed is a property of the paper (or other medium) and varies from paper type to paper type, and may also vary slightly within a given paper type or even on a given sheet depending on the formation properties of the light.

Given that optical dot gain changes in amount of reflected light from printed paper, optical dot gain plays an important role in visual characteristics of printed mediums. In particular, if accurate colour reproduction is required, then the effect of the optical dot gain for a particular medium needs to be accounted for. Typically, optical dot gain for a particular medium is accounted for by producing a colour calibration profile, such as an International Color Consortium (ICC) profile, for a given printer and print medium combination. The colour calibration profile is produced essentially by printing a large number of colour patches and experimentally determining what the effect of optical dot gain (and other processes) is for a printer and print medium combination. Such a process has the draw-back that it is necessary to produce a colour profile for every print media to be used with a given printer, and producing colour profiles is an expensive process both in terms of time and of equipment.

Another method for dealing with the effects of optical dot gain is to model the effect of optical dot gain for a given media. If this is possible, then it may be possible to produce a profile for a printer that is largely independent of the type of media that is being printed on. Optical dot gain is not the only important factor to understand to produce such a system. For example, gloss or surface roughness is another important property. However, if optical dot gain can be modelled then optical dot gain may be compensated for. In order to make use of effective models of optical dot gain, then the properties that give rise to optical dot gain ODG must be measured.

Optical dot gain also affects the sharpness of shapes and characters on printed documents. This sharpness is reflected in measurements of printer resolution, which measure the ability of a printing system to reproduce fine details. Optical dot gain changes these measurements of printer resolution by changing the amount of light that is reflected between and around lines printed on paper. So, for a fixed printing system, different paper types can lead to different measurements of resolution for the printing system, independent of the actual mechanism of the printing system. This is clearly an undesirable property for measurement of a printing system which should be independent of the paper type.

While printer resolution is one of the important printer quality metrics, there has not been any industry standard resolution metrics for digital printers. In the ISO/IEC 13660 (2001) image quality standard, no standardised measurements are related to printer resolutions. In printer resolution measurement, a common method of evaluating one dimensional resolution of the printer is a Contrast Transfer Function (CTF) measurement. The process of CTF measurement includes printing CTF patterns, which consists of black and white bar charts of varying spatial frequencies, imaging the CTF patterns and measuring the contrasts at the different spatial frequencies.

For a given imaging device, the CTF measured is actually the result of physical dot gain and optical dot gain combined. The physical dot gain is related to the printer and the printing process, while the optical dot gain is due to the optical scattering of light within the print media in the reflective imaging process. In order to precisely and repeatedly evaluate the resolution of a printer, it is desired to quantify the physical dot gain effect and the optical dot gain effect separately.

Typically, CTF measurement is performed by measuring the minimum (Dmin) and maximum (Dmax) optical densities of the black and white lines on the CTF patterns. The contrast, (Dmax−Dmin)/(Dmax+Dmin), at different spatial frequencies is commonly used as a resolution metric. But this resolution metric is by no means the only resolution metric of printers. Another known method is to use (Dmax−Dmin) as the resolution metric, as avoiding division by (Dmax+Dmin) is considered to be more representative of human perception.

Measurements of optical dot gain properties of different paper types have been performed for quite some time. There are a number of different conventional methods used to measure optical dot gain. In one such method, an image of an edge is projected on to a sheet of paper and the sharpness of the edge reflected off the paper is measured. In another method of measuring optical dot gain a laser spot is focussed onto a piece of paper and the distribution of light around the spot is measured using high-resolution imaging or a microdensitometer. In still another method, an image with patches of lines of different spacings may be printed on a medium. The printed medium may then be scanned across at high resolution to determine the profile of reflected light between the lines in order to infer parameters of some functional parameterisation of light scattering probability. For example, the light reflected from the medium may be measured using a one dimensional sensor scanned across the test pattern.

In still another method of measuring optical dot gain, images with patches of lines with different spacing are produced on stripping film. The film is placed in contact with a medium and then the medium is scanned at high resolution to infer parameters of some functional parameterisation of light scattering probability. Finally, in another method of measuring optical dot gain, an image of a patch of lines is projected onto a sheet of paper. The paper is then imaged through the patch of lines at high resolution to infer the parameters of some functional parameterisation of optical scattering probability.

The above optical dot gain measurement methods that directly measure the optical dot gain properties of the medium require expensive measurement apparatus, high resolution imaging. The above optical dot gain methods are also sensitive to noise and have poor reproducibility. The methods that infer the optical dot gain properties require high resolution imaging, and depend on the functional parameterisation of the optical dot gain.

The above methods of measuring printer resolution often give different results based on subtle properties of a print medium on which the test target is printed. Thus, a need clearly exists for a more efficient method of evaluating printer resolution which is largely independent of the paper being used.

SUMMARY OF THE INVENTION

It is an object of the present invention to substantially overcome, or at least ameliorate, one or more disadvantages of existing arrangements.

According to one aspect of the present invention there is provided a method of determining a light scattering property of a medium, said method comprising the steps of:

illuminating the medium through a test pattern, the test pattern comprising at least one region containing a first pattern with substantial variation in two orthogonal directions at one scale, the test pattern further comprising at least one other region containing the first pattern at a different scale, wherein a density of the at least one region is substantially the same as a density of the at least one other region;

measuring light reflected from the illuminated medium through the test pattern; and determining a light scattering property of the medium based on the measured light.

An apparatus for determining a light scattering property of a medium, said apparatus comprising:

illuminating device for illuminating the medium through a test pattern, the test pattern comprising at least one region containing a first pattern with substantial variation in two orthogonal directions at one scale, the test pattern further comprising at least one other region containing the first pattern at a different scale, wherein a density of the at least one region is substantially the same as a density of the at least one other region;

imaging device for measuring light reflected from the illuminated medium through the test pattern to capture an image of the illuminated medium; and processor for determining a light scattering property of the medium based on the measured light.

A computer readable medium, having a program recorded on the medium, where the program is configured to make a computer execute a process to determine a light scattering property of a medium, said program comprising:

code for illuminating the medium through a test pattern, the test pattern comprising at least one region containing a first pattern with substantial variation in two orthogonal directions at one scale, the test pattern further comprising at least one other region containing the first pattern at a different scale, wherein a density of the at least one region is substantially the same as a density of the at least one other region;

code for measuring the light reflected from the illuminated medium through the test pattern to capture an image of the illuminated medium; and code for determining a light scattering property of the medium based on the measured light.

A method of determining a resolution measurement for a printer based on a medium on which the printer prints, said method comprising the steps of:

illuminating an area of the medium through a test pattern, the test pattern comprising at least one region containing a first pattern with substantial variation in two orthogonal directions at one scale, the test pattern further comprising at least one other region containing the first pattern at a different scale;

measuring light reflected from the illuminated area of the medium through the test pattern;

determining a light scattering property of the area of the medium based on the measured light;

printing a second test pattern for determining printer resolution, on a second area of said medium;

determining resolution of said printer based on an image of said second test pattern; and correcting the determined resolution for said printer based on said light scattering property.

An apparatus for determining a resolution measurement for a printer based on a medium on which the printer prints, said apparatus comprising:

means for illuminating an area of the medium through a test pattern, the test pattern comprising at least one region containing a first pattern with substantial variation in two orthogonal directions at one scale, the test pattern further comprising at least one other region containing the first pattern at a different scale;

means for measuring light reflected from the illuminated area of the medium through the test pattern;

means for determining a light scattering property of the area of the medium based on the measured light;

means for printing a second test pattern for determining printer resolution, on a second area of said medium;

means for determining resolution of said printer based on an image of said second test pattern; and means for correcting the determined resolution for said printer based on said light scattering property.

A computer readable medium, having a program recorded on the medium, where the program is configured to make a computer execute a process to determine a light scattering property of a medium, said program comprising:

code for determining a resolution measurement for a printer based on a medium on which the printer prints, said method comprising the steps of code for illuminating an area of the medium through a test pattern, the test pattern comprising at least one region containing a first pattern with substantial variation in two orthogonal directions at one scale, the test pattern further comprising at least one other region containing the first pattern at a different scale;

code for measuring light reflected from the illuminated area of the medium through the test pattern;

code for determining a light scattering property of the area of the medium based on the measured light;

code for printing a second test pattern for determining printer resolution on a second area of said medium;

code for determining resolution of said printer based on an image of said second test pattern; and code for correcting the determined resolution for said printer based on said light scattering property.

Other aspects of the invention are also disclosed.

BRIEF DESCRIPTION OF THE DRAWINGS

Some aspects of the prior art and one or more embodiments of the present invention will now be described with reference to the drawings and appendices, in which.

DETAILED DESCRIPTION OF EMBODIMENTS OF THE INVENTION

Figure 1A:
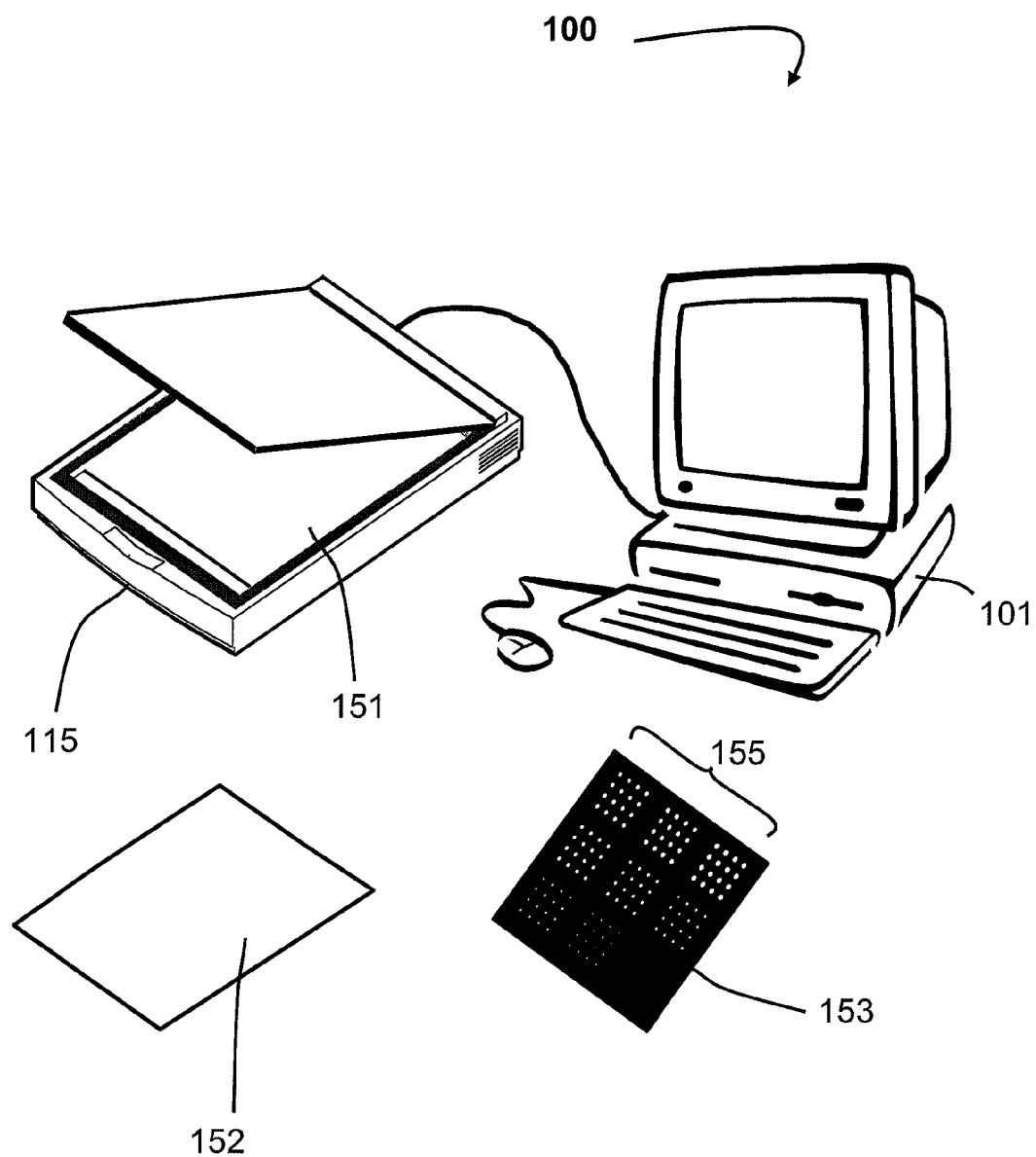
FIG. 1A is a schematic block diagram of a computer system upon which embodiments described can be practiced.

Where reference is made in any one or more of the accompanying drawings to steps and/or features, which have the same reference numerals, those steps and/or features have for the purposes of this description the same function(s) or operation(s), unless the contrary intention appears.

It is to be noted that the discussions contained in the "Background" section and that above relating to prior art arrangements relate to discussions of documents or devices which form public knowledge through their respective publication and/or use. Such should not be interpreted as a representation by the present inventor(s) or patent applicant that such documents or devices in any way form part of the common general knowledge in the art.

Overview

Optical dot gain as a probabilistic process was described above. The probability of light entering an unprinted medium at point x and being scattered and reemitted at a point y may be defined as probability function $p_s(x,y)$. Similarly the probability of light entering an unprinted medium and not returning due to absorption in the medium may be defined as probability function $p_a(x)$. Accordingly, any light that is not absorbed by the unprinted medium must be reemitted somewhere else in accordance with Equation (1) below:

$$\iint p_s(x,y)dy + p_a(x) = 1 \quad (1)$$

The probability functions $p_s(x,y)$ and $p_a(x)$ are actually functions of the wavelength of light, but that has been omitted for notational convenience.

The effect of optical dot gain on reflection from a print medium or from a surface with a transmission mask in contact with the surface of the medium may be modelled mathematically as a convolution followed by a masking step. If the transmission mask or print medium is described as a two dimensional function, $i(x)$, where the function is one (1), where the medium is fully transmissive and zero (0), and where the medium is fully opaque, then the scattered portion of a reflected image $r(x)$ may be modelled in accordance with Equation (2) below:

$$r(x) = i(x)\iint p_s(x,y)i(y)dy \quad (2)$$

One simplifying assumption that may be made is that the light scattering in a sheet of paper or other media is roughly homogeneous and isotropic within the sheet. This means that the above probability functions $p_s(x,y)$ and $p_a(x)$ are only functions of the distance between an entering point and an exit point, and not on their actual locations (i.e. $p_s(x,y) = p_s(|x-y|) = p_s(r)$).

Assuming only homogeneity, the reflected image $r(x)$ may be defined in accordance with Equation (3) below:

$$r(x,y) = i(x,y)(p_s(x,y) * i(x,y)) \quad (3)$$

where * denotes convolution, and vector notation has been replaced with a two dimensional representation in Cartesian coordinates, (x,y).

Value at Centre of Disk

An image function $i(r; s)$ that consists of a disc of radius s may be defined in accordance with Equation (4) as follows:

$$i(r;s) = \begin{cases} 1 & r < s \\ 0 & r > s \end{cases} \quad (4)$$

Reflectance of a medium at the centre of the disc may be defined in accordance with Equation (5) as follows:

$$r_0(s) = \int\int p_s(x,y) i(x,y) dx dy \quad (5)$$
$$= 2\pi \int_0^s p_s(r) r dr$$

If the reflectance of the medium at the centre of a number of discs of different radii is measured, then a scattering probability function may be determined in accordance with Equation (6) below:

$$p_s(s) = \frac{1}{2\pi s} \frac{\partial r_0(s)}{\partial s} \quad (6)$$

Mean Reflectance

The mean reflectance R from the surface of a medium may be determined in accordance with Equation (7) below $$R = \int\int r(x,y) dx dy \quad (7)$$
$$= \int\int i(x,y)(p_s(x,y) * i(x,y)) dx dy$$
$$= \int\int |I(u,v)|^2 P_s(u,v) du dv$$

where $I(u,v)$ and $P_s(u,v)$ are two-dimensional Fourier transforms of a transmission image and scattering probability function respectively, and Parseval's theorem has been applied.

If it is now assumed that the scattering function is isotropic as well as homogeneous then the mean reflectance of the surface of the medium may be defined in accordance with Equation (8) below:

$$R = \int\int |I(q,\theta)|^2 P_s(q) q dq d\theta \quad (8)$$

Consider now a transmission pattern that may be reproduced at different scales, so that $i(x,y;s) = i(sx,sy)$. The mean reflectance from different surfaces, as a function of scale, may be defined in accordance with Equation (9) below:

$$R(s) = \int\int |I(q/s,\theta)|^2 P_s(q) q dq d\theta \quad (9)$$

Changing variables to a logarithmic coordinate in scale gives Equation (10), below:

$$R(e^\rho) = \int\int |I(e^{\xi-\rho},\theta)|^2 P_s(e^\xi) e^{2\xi} de^\xi d\theta \quad (10)$$

Equation (10) shows that the mean reflectance off the surface of the medium as a function of scale is a convolution of the logarithmic transform of the scattering function Fourier transform and the logarithmic transform of the angular integral of the Fourier magnitude squared of the transmission image. Equation (10) also shows that if the mean reflectance function is determined as a function of scale, with the scale sampled using a logarithmic spacing, then the scattering function can be recovered from the sampled data using de-convolution methods.

The image function $i(r; s)$ which consists of a disc of radius s may be defined in accordance with Equation (11) below:

$$i(r;s) = \begin{cases} 1 & r < s \\ 0 & r > s \end{cases} \quad (11)$$

Equation (11) has a Fourier transform defined according to Equation (12) below:

$$I(q;s) = \frac{sJ_1(2\pi sq)}{q} \quad (12)$$

and the mean reflectance as a function of scale is defined according to Equation (13) below:

$$R(s) = 2\pi s^2 \int \frac{J_1^2(2\pi sq) p_s(q)}{q} dq \quad (13)$$

Figure 10:
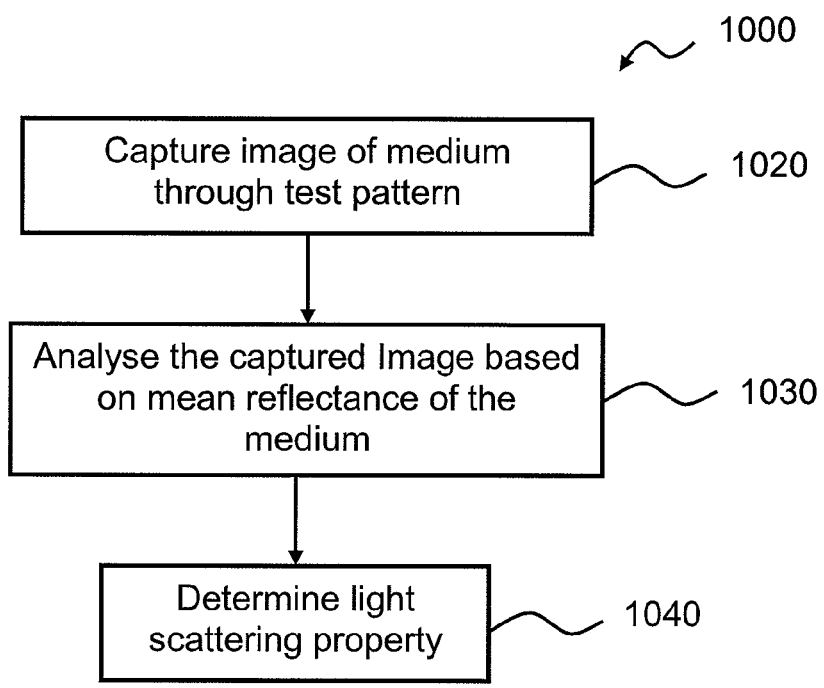
FIG. 10 is a flow diagram showing a method of determining a light scattering property of a medium according to the second embodiment.

A method 300 (see FIG. 3) of determining a light scattering property of a print medium 152, according to a first embodiment, will be described below with reference to FIGS. 1A to 4 and FIG. 9. Another method 1000 (see FIG. 10) of determining a light scattering property of the medium 152, according to a second embodiment, will be described below with reference to FIGS. 5 to 8 and FIG. 10. Further, a method 1100 of measuring printer resolution will also be described with reference to FIGS. 11 to 20.

Figure 1B:
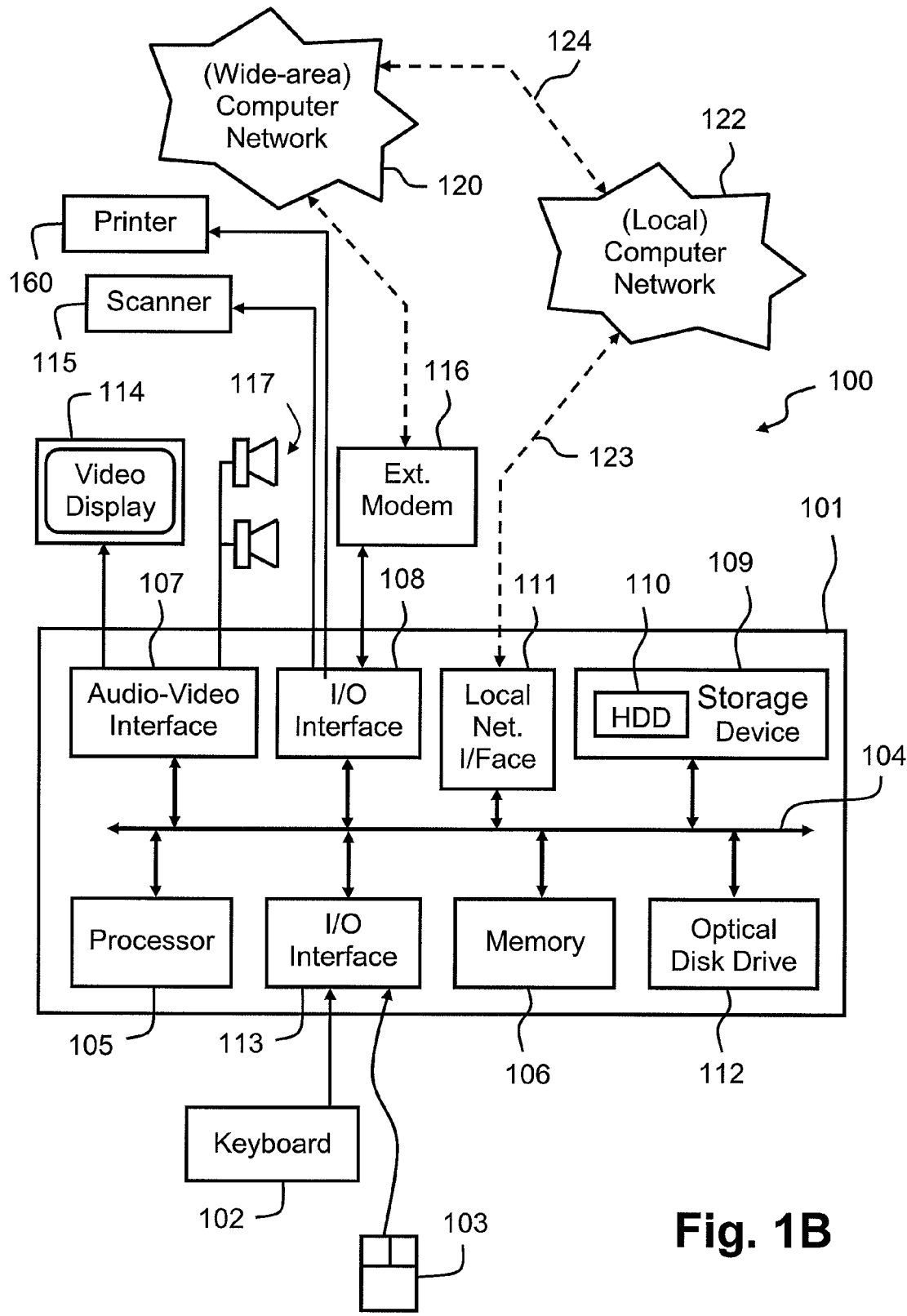
FIG. 1B shows the computer system of FIG. 1A in more detail.

The methods 300, 1000 and 1100, and other methods described herein, may be implemented using a computer system 100, as shown in FIGS. 1A and 1B, wherein the processes of FIGS. 2 to 20 may be implemented as software, such as one or more application programs executable within the computer system 100. In particular, the steps of the described methods are effected by instructions in the software that are carried out within the computer system 100. The instructions may be formed as one or more code modules, each for performing one or more particular tasks. The software may also be divided into two separate parts, in which a first part and the corresponding code modules performs the described methods and a second part and the corresponding code modules manage a user interface between the first part and the user. The software may be stored in a computer readable medium, including the storage devices described below, for example.

The software is loaded into the system 100 from the computer readable medium, and then executed by the system 100. A computer readable medium having such software or computer program recorded on it is a computer program product. The use of the computer program product in the computer system 100 preferably effects an advantageous apparatus for implementing the described methods.

As seen in FIG. 1A, the computer system 100 for use in determining a light scattering property of the medium 152 comprises a processing device in the form of a computer module 101 and an imaging device in the form of a scanner 115. The computer system 100 also includes a printer 160.

A transmission mask 153, according to the first embodiment, for placing in contact with the medium 152, is also shown in FIG. 1A. As seen in FIG. 1A, the transmission mask 153 comprises an opaque area with a plurality of circular holes formed in the mask 153. The circular holes are of different sizes and form a pattern 155. The pattern 155 will be referred to below as a "test pattern". The transmission mask 153 will be described in further detail with reference to FIG. 4.

FIG. 1B shows the computer system 100 in more detail. As seen in FIG. 1B, the computer system 100 is formed by the computer module 101, input devices such as a keyboard 102 and a mouse pointer device 103, and output devices including the scanner 115, the printer 160, a display device 114 and loudspeakers 117. An external Modulator-Demodulator (Modem) transceiver device 116 may be used by the computer module 101 for communicating to and from a communications network 120 via a connection 121. The network 120 may be a wide-area network (WAN), such as the Internet or a private WAN. Where the connection 121 is a telephone line, the modem 116 may be a traditional "dial-up" modem. Alternatively, where the connection 121 is a high capacity (e.g., cable) connection, the modem 116 may be a broadband modem. A wireless modem may also be used for wireless connection to the network 120.

The computer module 101 typically includes at least one processor unit 105, and a memory unit 106 for example formed from semiconductor random access memory (RAM) and read only memory (ROM). The module 101 also includes a number of input/output (I/O) interfaces including an audio-video interface 107 that couples to the video display 114 and loudspeakers 117, an I/O interface 113 for the keyboard 102 and mouse 103 and optionally a joystick (not illustrated), and an interface 108 for the external modem 116, the printer 160 and scanner 115. In some implementations, the modem 116 may be incorporated within the computer module 101, for example within the interface 108. The computer module 101 also has a local network interface 111 which, via a connection 123, permits coupling of the computer system 100 to a local computer network 122, known as a Local Area Network (LAN). As also illustrated, the local network 122 may also couple to the wide network 120 via a connection 124, which would typically include a so-called "firewall" device or similar functionality. The interface 111 may be formed by an Ethernet™ circuit card, a wireless Bluetooth™ or an IEEE 802.11 wireless arrangement.

The interfaces 108 and 113 may afford both serial and parallel connectivity, the former typically being implemented according to the Universal Serial Bus (USB) standards and having corresponding USB connectors (not illustrated). Storage devices 109 are provided and typically include a hard disk drive (HDD) 110. Other devices such as a floppy disk drive and a magnetic tape drive (not illustrated) may also be used. An optical disk drive 112 is typically provided to act as a non-volatile source of data. Portable memory devices, such optical disks (eg: CD-ROM, DVD), USB-RAM, and floppy disks for example may then be used as appropriate sources of data to the system 100.

The components 105 to 113 of the computer module 101 typically communicate via an interconnected bus 104 and in a manner which results in a conventional mode of operation of the computer system 100 known to those in the relevant art. Examples of computers on which the described arrangements can be practised include IBM-PC's and compatibles, Sun Sparcstations, Apple Mac™ or alike computer systems evolved therefrom.

Typically, the application programs discussed above are resident on the hard disk drive 110 and read and controlled in execution by the processor 105. Intermediate storage of such programs and any data fetched from the networks 120 and 122 may be accomplished using the semiconductor memory 106, possibly in concert with the hard disk drive 110. In some instances, the application programs may be supplied to the user encoded on one or more CD-ROM and read via the corresponding drive 112, or alternatively may be read by the user from the networks 120 or 122. Still further, the software can also be loaded into the computer system 100 from other computer readable media. Computer readable media refers to any storage medium that participates in providing instructions and/or data to the computer system 100 for execution and/or processing. Examples of such media include floppy disks, magnetic tape, CD-ROM, a hard disk drive, a ROM or integrated circuit, a magneto-optical disk, or a computer readable card such as a PCMCIA card and the like, whether or not such devices are internal or external of the computer module 101. Examples of computer readable transmission media that may also participate in the provision of instructions and/or data include radio or infra-red transmission channels as well as a network connection to another computer or networked device, and the Internet or Intranets including e-mail transmissions and information recorded on Websites and the like.

The second part of the application programs and the corresponding code modules mentioned above may be executed to implement one or more graphical user interfaces (GUIs) to be rendered or otherwise represented upon the display 114. Through manipulation of the keyboard 102 and the mouse 103, a user of the computer system 100 and the application may manipulate the interface to provide controlling commands and/or input to the applications associated with the GUI(s).

The described methods may alternatively be implemented in dedicated hardware such as one or more integrated circuits performing the functions or sub functions of the methods. Such dedicated hardware may include graphic processors, digital signal processors, or one or more microprocessors and associated memories.

Figure 2:
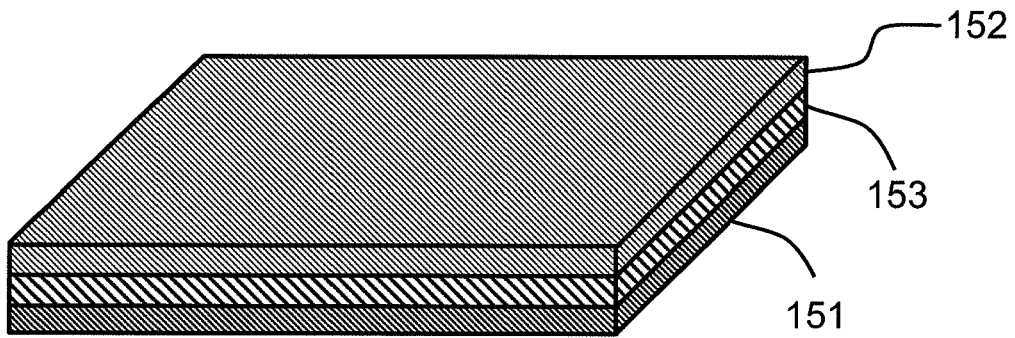
FIG. 2 shows relative placement of a medium, a transmission mask and the surface of a platen of a scanning device.

To measure the light scattering properties of the print medium 152, the transmission mask 153 is placed on the scanner platen 151 in contact with the medium 152, as illustrated in FIG. 2. As will be described below, in the first embodiment, the transmission mask 153 is produced with a patterned surface of polymer on a glass substrate. The patterned surface of the substrate is placed in contact with the medium 152 to be measured.

Figure 3:
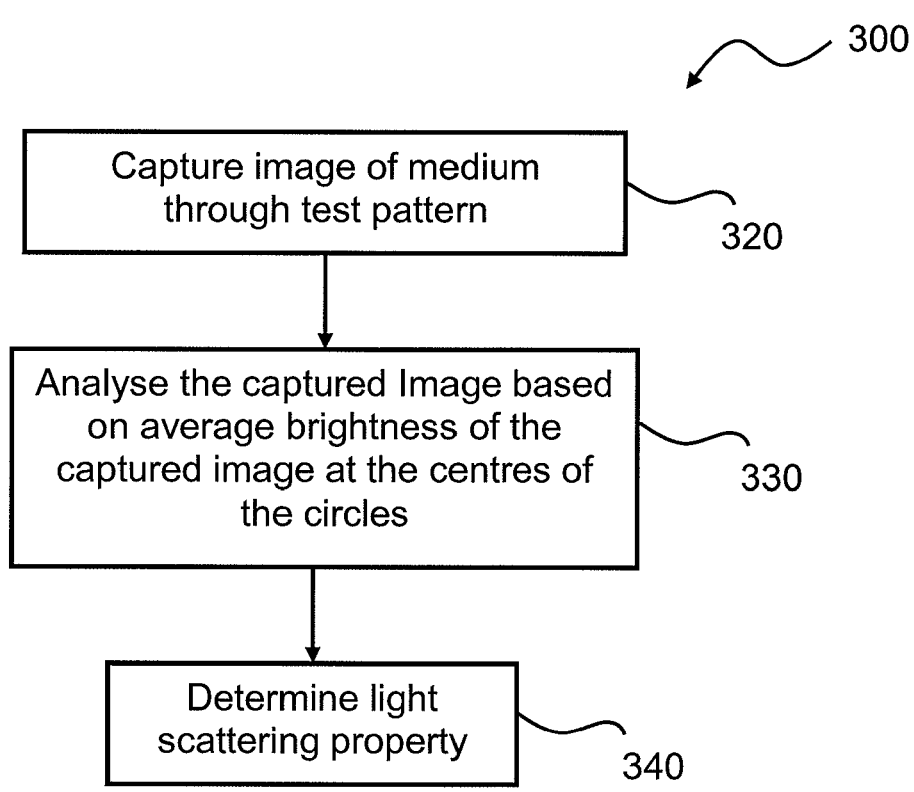
FIG. 3 is a flow diagram showing a method of determining a light scattering property of a medium according to a first embodiment.

The method 300 of determining a light scattering property of the medium 152 will now be described in more detail with reference to FIG. 3.

After the medium 152 and the transmission mask 153 have been placed on to the scanner platen 151, as seen in FIG. 2, the method 300 begins at a first step 320, where an image of the medium 152, through the test pattern 155 formed by the transmission mask 153, is captured by the scanning device 115. In order to capture the image, the scanning device 115 performs the sub-steps of illuminating the medium 152 through the test pattern 155 and then measuring light reflected from the illuminated medium 152 through the test pattern 155.

The image captured at step 320 is preferably stored, as an image file, in memory 106 and/or the hard disk drive 110, in an uncompressed format. The image is preferably captured at step 320 with all image processing features of the scanner 115, such as unsharp masking, turned off. Such scans are typically taken at a predetermined resolution (e.g., 2400 dpi).

Figure 4:
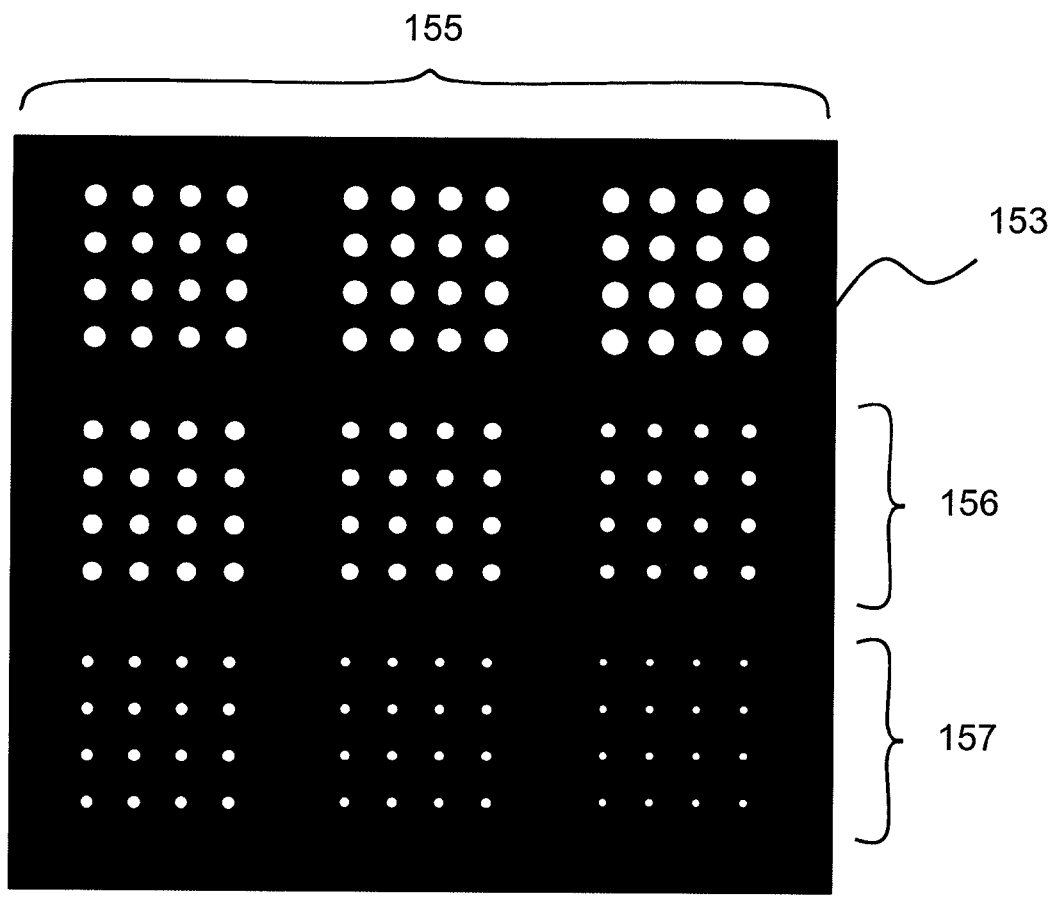
FIG. 4 shows a representation of a portion of a transmission mask used in the method of FIG. 3.

In step 330, the processor 105 accesses the image captured at step 320 from memory 106 and analyses the image to produce data that can be used to determine the light scattering property. In this connection, FIG. 4 shows a representation of the test pattern 155 formed by the mask 153 in more detail. As shown in FIG. 4, the mask 153 comprises an opaque area with a number of circles of different sizes excised from the opaque area to form the test pattern 155. The opaque area of the mask 153 is of a predetermined size and in one embodiment is one-hundred (100) mm square.

The layout of the mask 153 shown in FIG. 4 is illustrative only. The opaque area of the mask 153 is preferably divided into sixteen (16) square regions each 25 mm to a side. However, it was not possible to fully show the mask 153 with the sixteen (16) square regions due to the size of the holes in each of the square regions of the mask 153, as will be described below. Accordingly, the mask 153 shown in FIG. 4 is only divided into nine (9) square regions.

Each of the square regions of the mask 153 comprises an array of circular holes with no absorptive material, allowing transmission of light through the mask 153 inside each of the circles. In a given square region of the mask 153, all of the circles have the same radius. The circles within each of the square regions are arranged in a 4×4 grid, with centres spaced by a predetermined distance (e.g., 5 mm) apart. The size of circles in different ones of the square regions of the mask 153 is different. Each of the square regions of the transmission mask 153 has the same pattern albeit of different scale with different size circular holes in each particular region. As seen in FIG. 4, the pattern of each square region comprises circles allowing for substantial variation in light transmission in two orthogonal directions at a particular scale.

Accordingly, the regions of the transmission mask 153 form a test pattern 155 comprising at least one region (e.g., 156) containing a first pattern with substantial variation in light transmission in two orthogonal directions at one scale. The test pattern 155 further comprises at least one other region (e.g., 157) containing the first pattern at a different scale.

In one embodiment, the radius of the circles in each of the sixteen (16) regions of the mask 153 is forty (40) microns, fifty-two (52) microns, sixty-seven (67) microns, eighty-seven (87) microns, one-hundred and fourteen (114) microns, one-hundred and forty-seven (147) microns, one-hundred and ninety-one (191) microns, two-hundred and forty-eight (248) microns, three-hundred and twenty-two (322) microns, four-hundred and eighteen (418) microns, five-hundred and forty-two (542) microns, seven-hundred and four (704) microns, nine-hundred and fifteen (915) microns, one point nineteen (1.19) mm, one point five four (1.54) mm, and two (2) mm, respectively.

The sizes of the circular holes in each of the regions of the mask 153, as described directly above, are roughly logarithmically spaced between forty (40) microns and two (2) mm.

Many other distributions of radii for the holes in the mask 153 are possible and the selection of the radius of the holes in each of the square regions is not essential.

The transmission mask 153 may also contain fiducial marks such as crosses or spirals in a fixed geometric relationship to allow convenient locations of the circles on an image of the mask 153. Alternately, the mask 153 may be placed in a fixed physical location with respect to the scanner platen 151. In one embodiment, the mask 153 may be manufactured onto the platen 151 of the scanner 115.

Construction of the mask 153 may be achieved using a photolithographic process. In one embodiment, the mask substrate is quartz and has a black polymer substance written on to the mask 153. The black polymer substance is a photosensitive polymer and may be written at micron resolution using a direct laser-writing machine, as known in the art.

Returning to FIG. 3, as described above, at step 330 the image captured at step 320 is analysed by the processor 105. During the analysis, if fiducial marks have been placed on the transmission mask 153, the processor 105 locates the fiducial marks and uses the fiducial marks to determine where the centres of each of the circles on the mask 153 are within the captured image. For each square region containing the same size circles, RGB values of pixels at the centres of the circles of the same size are averaged to determine an average brightness of the captured image at the centre of the circles.

The method 300 continues at the next step 340, where the processor 105 performs the step of determining the light scattering property of the medium 152 from the captured image stored in the memory 106 and/or hard disk drive 110, based on the average brightness of the captured image at the centre of the circles as determined at step 330. A method 900 of determining the light scattering property of the medium 152 based on the average brightness of the captured image at the centre of the circles, as executed at step 340, will now be described with reference to FIG. 9. The method 900 may be implemented as software resident on the hard disk drive 110 and being controlled in its execution by the processor 105.

The method 900 begins at step 901, where a pair of values $(r_i, b_i)$ consisting of the radius $r_i$ of the circles for one of the square regions of circles and the average brightness $b_i$ of the captured image of the medium 152 at the centre of the circles for that square region of circles, is determined by the processor 105 for each square region of circles. The pair of values $(r_i, b_i)$ are stored in the memory 106. Then at the next step 903, the processor 105 fits a smooth function through each of the points represented by the values $(r_i, b_i)$ as a function of the radius for each point. In accordance with the first embodiment, the smooth function is a polynomial of order six. This function may be denoted as $\hat{f}(r)$. Accordingly, the light scattering property of the medium 152 is determined in accordance with Equation (14) below:

$$p_s(r) = \frac{1}{2\pi r} \frac{\partial \hat{f}(r)}{\partial r} \tag{14}$$

The result of step 903 is stored in the memory 106.

If the points represented by the values $(r_i, b_i)$ are close enough together, then the light scattering property of the medium 152 may be determined by determining a difference between the measured light value, $b_i$, of adjacent points.

Figure 5:
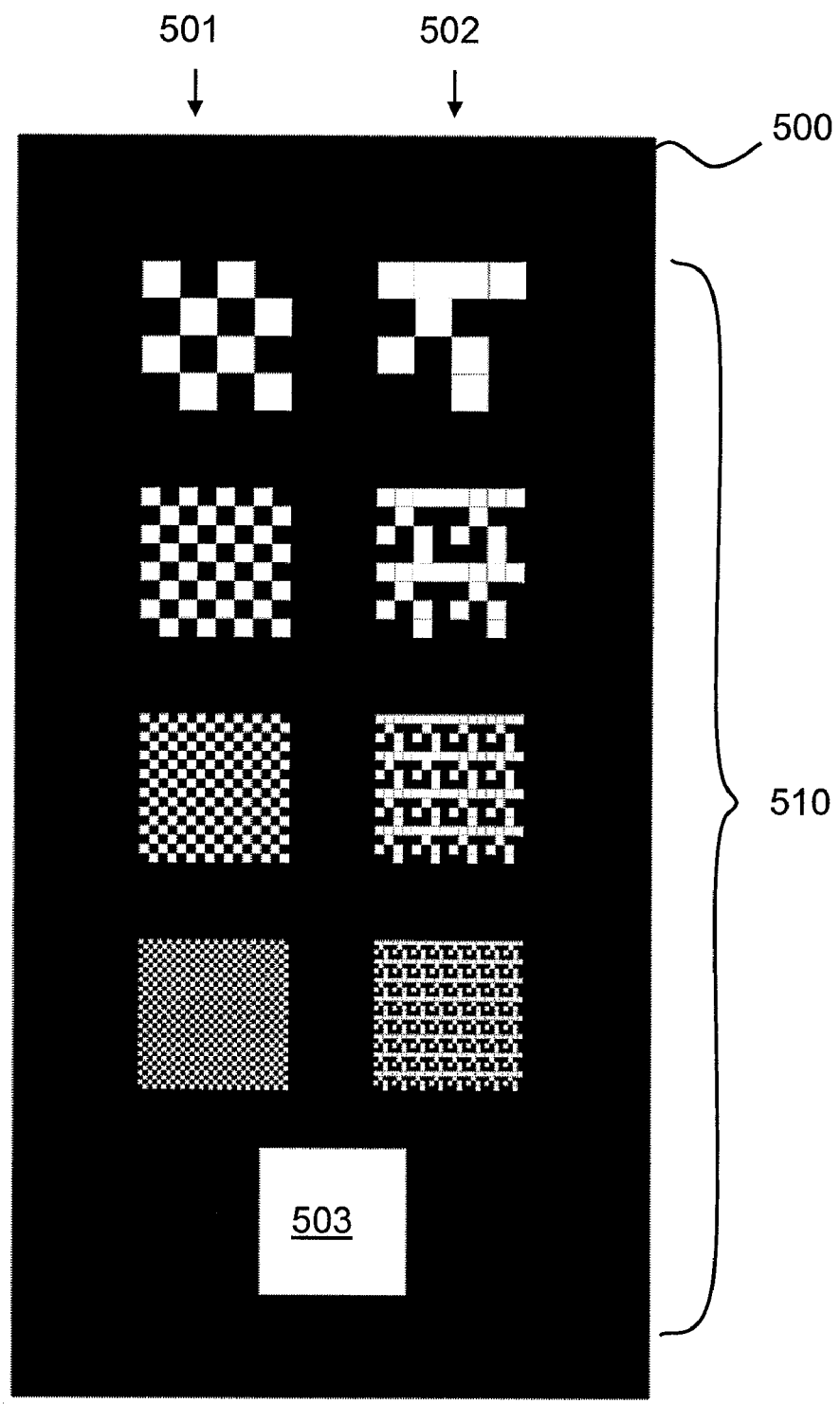
FIG. 5 shows a transmission mask according to a second embodiment.

FIG. 5 shows an alternative transmission mask 500 according to a second embodiment. The transmission mask 500 comprises nine patches arranged in two sets of patches 501 and 502, and a plain patch 503 as shown in FIG. 5. Each of the sets of patches 501 and 502 has a corresponding pattern. The pattern is repeated in each patch of a particular one of the sets 501 and 502 with each patch having a different scale. Each of the patches in the sets 501 and 502 has substantially the same density. The arrangement of patches formed by the transmission mask 500 forms a test pattern 510, as seen in FIG. 5

Figure 6:
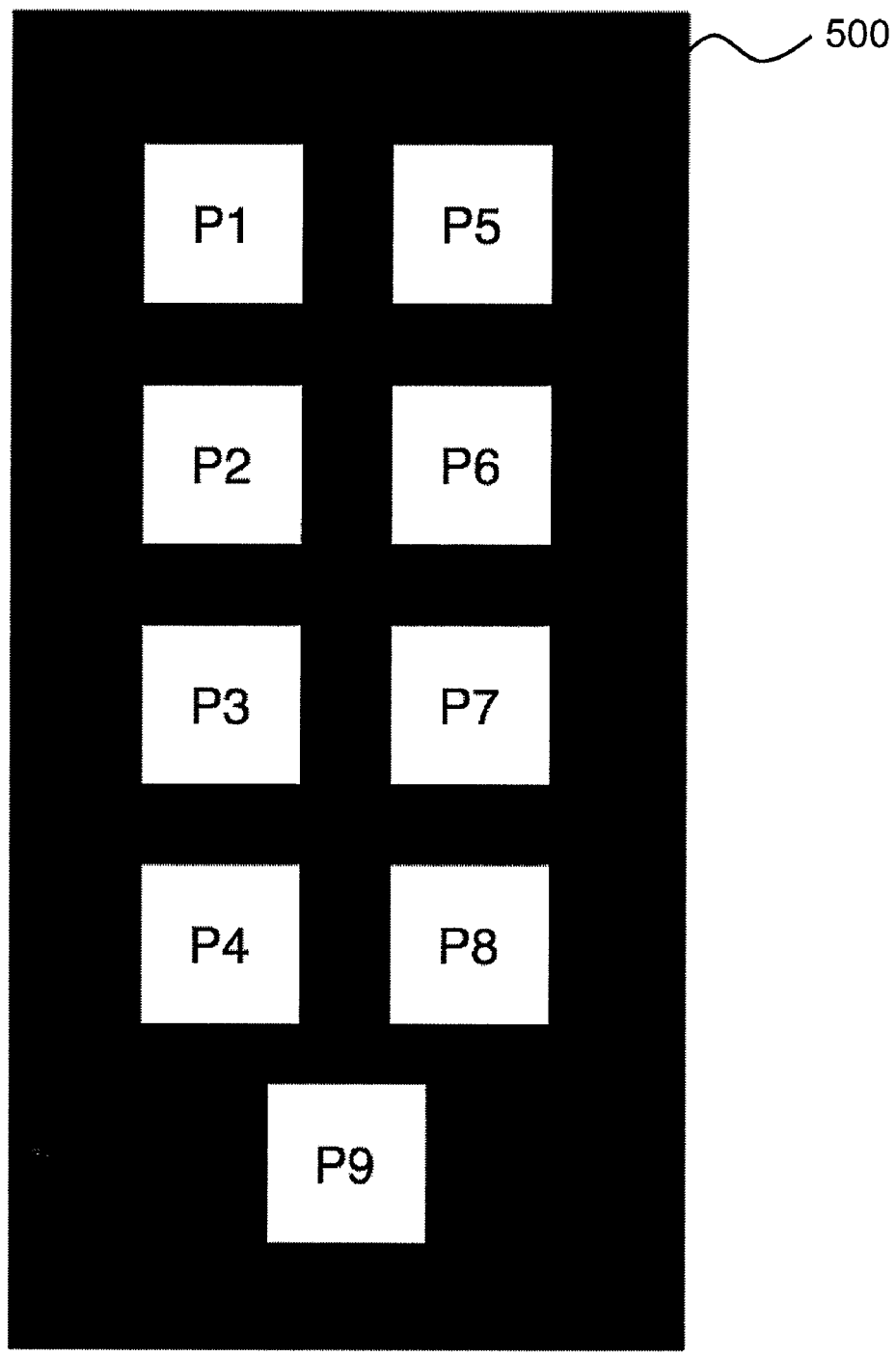
FIG. 6 shows a layout of patches of the transmission mask of FIG. 5.
Figure 7A:
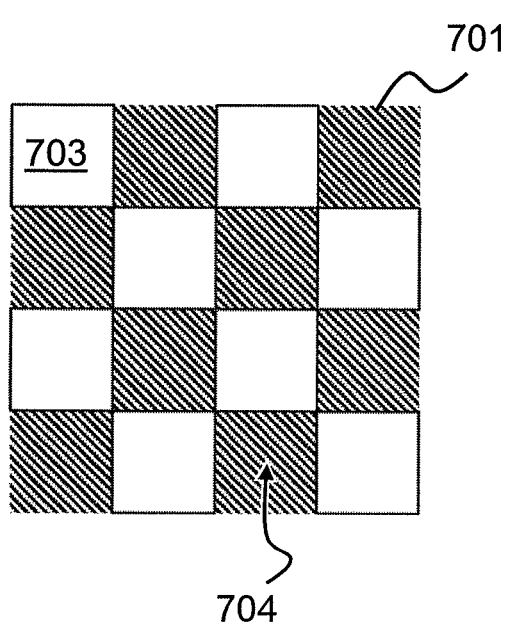
FIG. 7A shows a pattern used in the transmission mask of FIG. 5.

FIG. 6 shows the locations of the nine patches on the transmission mask 500. Patches P1 to P4 make up the set of patches 501. Each of the patches P1 to P4 has a first pattern 701 as shown in FIG. 7A, with the pattern 701 being replicated at different scales within a boundary of each patch P1 to P4. Each of the patches P1 to P4 has substantially the same density.

Figure 7B:
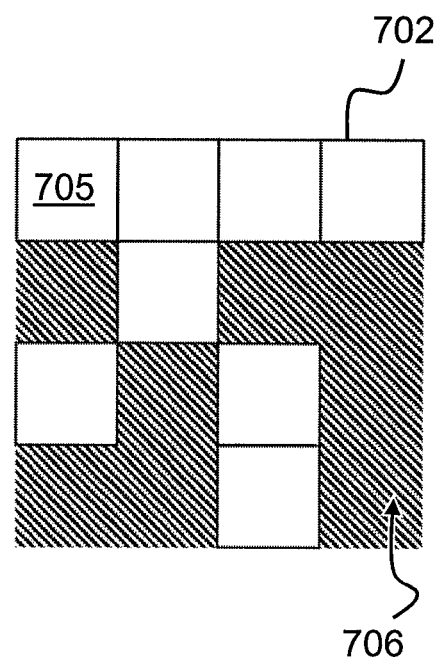
FIG. 7B shows a pattern used in the transmission mask of FIG. 5.

Patches P5 to P8 make up the set of patches 502. Each of the patches P5 to P8 has a pattern 702 as shown in FIG. 7B, with the pattern 702 being replicated at different scales within a boundary of each patch P5 to P8. Each of the patches P5 to P8 has substantially the same density. The size of the features in FIGS. 5, 6 and 7 is illustrative only. Each of the patches P1 to P9 has a predetermined size which in one embodiment is 20 mm by 20 mm. The size of the individual squares (e.g., 703) in each pattern 701 and 702 also has a predetermined size.

In one embodiment, the size of each square in patch P1, patch P2, patch P3 and patch P4 is two-hundred (200) microns, one-hundred (100) microns, fifty (50) microns, and twenty five (25) microns, respectively. Similarly, the size of each square in patch P5, patch P6, patch P7 and patch P8 is two-hundred (200) microns, one-hundred (100) microns, fifty (50) microns, and twenty five (25) microns, respectively. Other arrangements and sizes of the patches P1 to P9 and the squares within each patch are possible.

Each of the patterns 701 and 702 has 50% transmission. That is, 50% of the individual squares (e.g., 703) in the pattern 701 allow light to be transmitted through the square, while the other 50% of the squares (e.g., 704) are opaque and absorb any light. Similarly, 50% of the individual squares (e.g., 705) in the pattern 702 allow light to be transmitted through the square, while the other 50% of the squares (e.g., 706) are opaque and absorb any light. Accordingly, the first and second pattern have substantially equal mean transmittance. Other transmission amounts for the patterns 701 and 702 are possible, and it is possible for the two patterns to have different transmission percentages.

As seen in FIG. 7A, the first pattern 701 has substantial variation in light transmission in two orthogonal directions. The test pattern 510 comprises the first set of patches 501 comprising at least one region containing the first pattern 701 with substantial variation in two orthogonal directions at one scale. The first set of patches 501 further comprises at least one other region containing the first pattern 701 at a different scale. The test pattern 510 also comprises the second set of patches 502 comprising at least other region containing the second pattern 702 at one scale. The second set of patches 502 also comprises at least one other region containing the second pattern at a different scale.

The ninth patch P9 of the transmission mask 500 is clear and allows direct reflectance of the medium 152 to be measured for reference. The transmission mask 500 may be manufactured according to the same manufacturing processes described above.

A method 1000 of determining a light scattering property of the medium 152, according to a second embodiment, will now be described in more detail with reference to FIG. 3. The method 1000 may be implemented as software resident on the hard disk drive 110 and being controlled in its execution by the processor 105.

Again, after the medium 152 and the transmission mask 500 have been placed on to the scanner platen 151, in the same manner as the transmission mask 153 seen in FIG. 2, the method 1000 begins at a first step 1020, where the scanning device 115 captures an image of the medium 152, through the test pattern 510 formed by the patches P1 to P9 of the transmission mask 500. The scanning device 115 captures the image by illuminating the medium 152 through the test pattern 510 formed by the patches of the transmission mask 500 and then measuring light reflected from the illuminated medium through the test pattern 510. The image captured at step 1020 is preferably stored in memory 106 and/or the hard disk drive 110, in an uncompressed format. Again, the image is preferably captured at step. 1020 with all image processing features of the scanner 115, such as unsharp masking, turned off.

In step 1030, the processor 105 accesses the image captured at step 1020 from memory 106 or the hard disk drive 110 and analyses the image to produce data that can be used to determine the light scattering property for the medium 152. In the method 1000, each part of the captured image that corresponds to a single patch (e.g., P1) on the transmission mask 500 is averaged to determine a mean reflectance of the medium 152 through the transmission mask 500. The mean reflectance of the patches P1 to P9 may be denoted $P_1 \ldots P_9$, where $P_9$ denotes the mean reflectance of the purely transmissive patch P9. Relative reflectance $R_i$ of each of the patches with a transmission pattern may be determined in accordance with Equation (15) as follows:

$$R_i = P_i/P_9 \qquad (15)$$

Due to the fact that the optical dot gain affects regions closer to edges more than regions further from edges, then the mean reflectance $P_1 \ldots P_9$ of the patches P1 to P9 at different scales and with different patterns will be different, although the transmission of each patch is the same. The differences in the mean reflectance for each of the patches P1 to P9 are used to constrain a model of the paper modulation transfer function of Equation (16) below and thereby constrain the model of the light scattering in the medium 152.

The method 1000 continues at the next step 1040, where the processor 105 performs the step of determining the light scattering property for the medium 152 from the image based on the analysis performed at step 1203. In step 1040, the modulation transfer function of the medium 152 is modelled in accordance with Equation (16) below:

$$M(u) = \frac{1}{(1 + k^2 u^2)^n} \qquad (16)$$

where k and n are constants that characterise the optical transfer properties of the medium 152. Also in step 1040, the effect of the optical dot gain on the reflection of the patterns on the transmission mask 500 is simulated and compared to the measured results from the analysis step 1030. If the simulation as applied to patch $P_i$ is denoted by $S_i(k,n)$, where k and n are the parameters of the paper modulation transfer function, then in step 1040, the values of k and n that produce the best match between the simulated results and the measured results are considered to be the best parameters for characterising the light scattering of the medium 152 under the transmission mask 500. The best match values for k and n are determined by solving Equation (17) below:

$$\min_{k,u} \sum_{i=1}^{8} (S_i(k, u) - R_i)^2 \quad (17)$$

which may be solved using any known numerical minimisation method that does not need analytic derivatives, such as Brent's method, which is well known in the art. The best match values for k and n determined in step 1040 are stored in the memory 106 and/or the hard disk drive 110.

Figure 8:
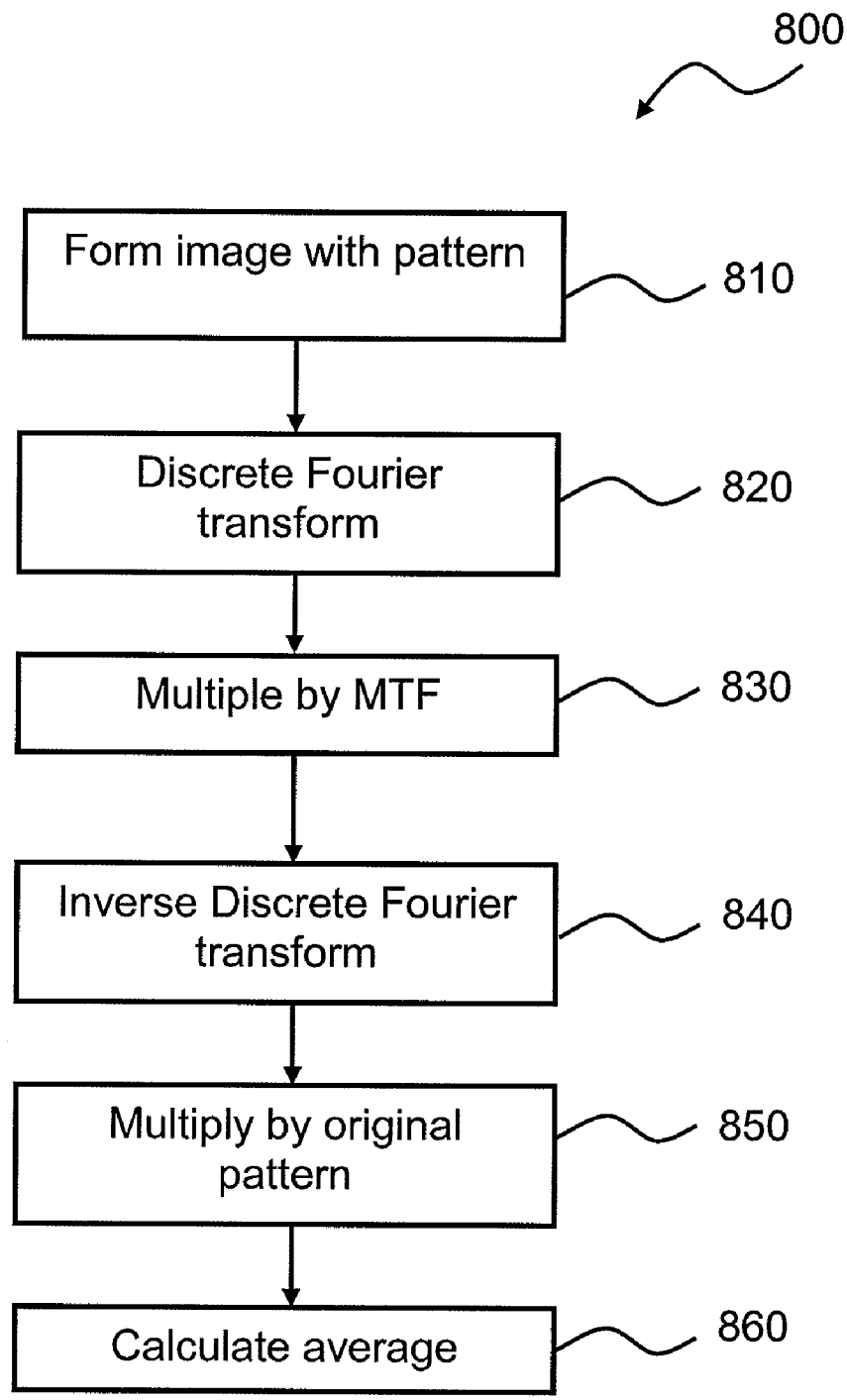
FIG. 8 is a flow diagram showing a method of simulating the effect of optical dot gain on the reflection of patterns of the transmission mask of FIG. 5, as executed in the method of FIG. 10.
Figure 9:
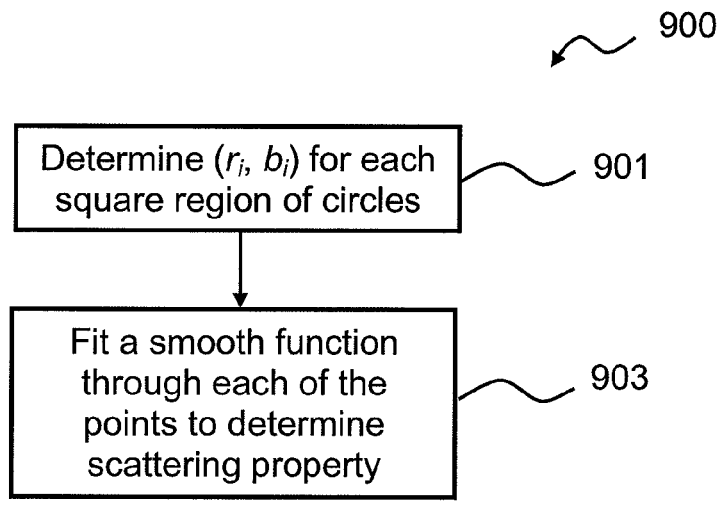
FIG. 9 is a flow diagram showing a method of determining the light scattering property of the medium based on the average brightness of the captured image at the centre of circles of the transmission mask of FIG. 4, as executed in the method of FIG. 3.

A method 800 of simulating the effect of the optical dot gain on the reflection of the patterns of the transmission mask 500, as executed at step 1040, will be now be described with reference to FIG. 8. The method 800 may be implemented as software resident on the hard disk drive 110 and being controlled in its execution by the processor 105. The method 800 is executed for each patch P1 to P8.

For a given patch P1, the method 800 begins at step 810, where the processor 105 uses the image captured at step 1020 to form an image with the pattern for that patch. The image that is formed is generally a high resolution version of a portion of the captured image containing the patch, with a predetermined number (e.g., ten (10)) pixels for each black or white square in the patch. The image that is formed at step 810 may be referred to as a patch transmission image. The patch transmission image is stored in the in the memory 106 and/or the hard disk drive 110.

In step 820, the patch transmission image is transformed by the processor 105 using a discrete 2D Fourier transform. The result of step 820 is stored in the memory 106 and/or the hard disk drive 110.

Then in step 830, the result of the Fourier transform stored in memory 106 and/or the hard disk drive 110 at step 820 is multiplied by the paper modulation transfer function M(u) given by Equation (16) above to determine a multiple Fourier transform. The multiple Fourier transform determined at step 830 is stored in memory and/or the hard disk drive 110.

In step 840, the processor 105 performs an inverse 2D Fourier transform on the multiple Fourier transform determined in step 830. Steps 810, 820, 830, and 840 together perform a digital convolution of the patch pattern with the inverse transform of the paper modulation transfer function (i.e., the paper point spread function). The result of steps 810, 820, 830 and 840 is a convolved image which is stored in the memory 106 and/or the hard disk drive 110.

The method 800 continues in step 850, where the processor 105 multiplies the convolved image by the patch transmission image formed in step 810 and the result of step 850 is then averaged in step 860 to determine the simulated mean reflectance of the patch including the effect of the paper modulation transfer function. The simulated mean reflectance of the patch, as determined at step 860, is stored in the memory 106 and/or the hard disk drive.

Application to Printer Resolution Measurement

Figure 11:
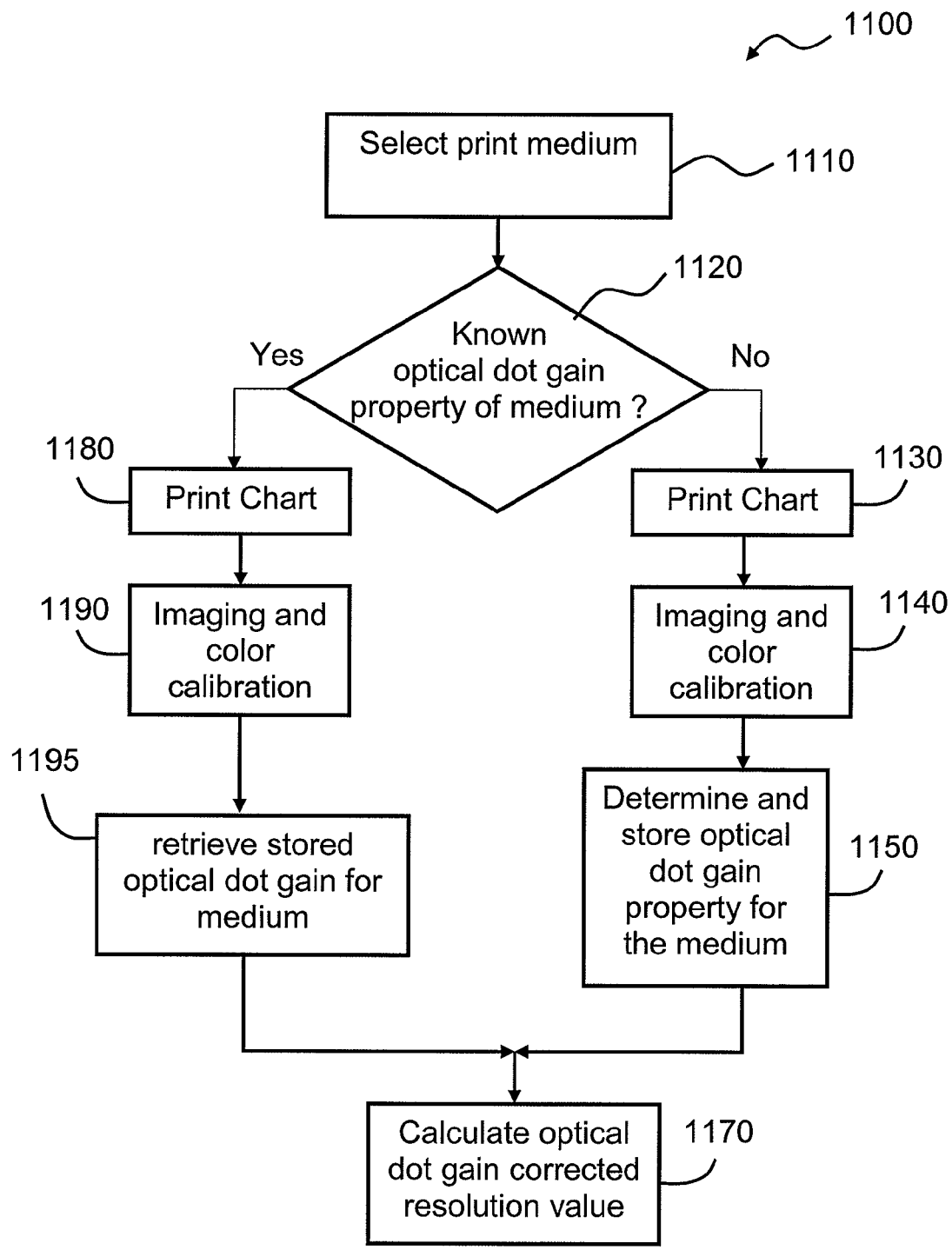
FIG. 11 is a flow diagram showing a method of measuring printer resolution.

FIG. 11 is a schematic flow diagram showing a method 1100 of measuring printer resolution. The method 1100 utilises the method 300 described above. One or more steps of the method 1100 may be implemented as software resident in the hard disk drive 110 and being controlled in its execution by the processor 105.

The method 1100 begins with step 1110 where a print medium of a specific type is selected. For example, the print medium may be Canon Photo Paper Pro™ or on Canon™ 80 g/m² plain paper. Other paper types can also be used.

At step 1120, if the processor 105 determines that the type of print medium (or paper) selected at step 1110 has previously had an optical dot gain property (i.e., a light scattering property), determined for the selected print medium, then the method 1100 proceeds to step 1180. Otherwise, the method 1100 proceeds to step 1130. The optical dot gain property for the selected print medium may be stored in the memory 106 and/or the hard disk drive 110. Accordingly, at step 1120, the processor 105 searches the memory 106 and hard disk drive 110 to make the determination.

At step 1130, the processor 105 sends a signal to the printer 160 and the printer 160 prints a first test chart 1200 (see FIG. 12) on a piece of print medium of the selected type. The specific details of the first test chart 1200 printed at step 1130 are described below. The type of print medium (or paper) selected at step 1110 may need to be fed into the printer 160.

After printing the first test chart 1200 is placed on the scanner 115. Then in step 1140, the processor 105 sends a signal to the scanner 115 and the printed test chart 1200 is imaged. The scanner 115 may be a flatbed scanner. Alternatively, another imaging device such as a camera or microscope may be used.

The image data representing the first test chart 1200 as captured by the scanner 115 at step 1140 may be stored in the memory 106 or the hard disk drive 110. Also at step 1140, the processor 105 adjusts the captured image data to be linear with reflected luminance. For example, the processor 105 may apply an International Color Consortium (ICC) input colour profile for the scanner 115 to adjust the captured image data.

At the next step 1150, the optical dot gain property (i.e., the light scattering property) of the print medium, upon which the first test chart 1200 was printed at step 1130, is determined by the processor 105 according to the method 300 described above. The optical dot gain property determined at step 1150 is stored in the memory 106. The determined optical dot gain property is stored on the hard disk drive 110 for later use with print media of the selected type. Step 1150 will be described in further detail below.

At the next step 1170, the processor 105 determines resolution of the printer 160. The determined resolution is corrected according to the optical dot gain property of the print medium as determined in step 1150. Step 1170 will be described in further detail below. A method 2000 of determining the resolution of the printing device 160, as executed at step 1170, will be described below with reference to FIG. 20.

As described above, at step 1120, if there was a previously stored optical dot gain) property for the selected type of print medium, then the method 1100 proceeds to step 1180. At step 1180, the processor 105 sends a signal to the printer 160 and the printer 160 prints a second test chart 1800 (see FIG. 18) on a piece of print medium of the selected type. The specific details of the second test chart 1800 printed at step 1180 are described below.

After printing, the second test chart 1800 is placed on the scanner 115. Then in step 1190, the processor 105 sends a signal to the scanner 115 and the printed second test chart 1800 is imaged. Image data, representing the second test chart 1800, captured by the scanner 115 may be stored in the memory 106 or the hard disk drive 110. Also at step 1190, the processor 105 adjusts the captured image data to be linear with reflected luminance. Again, the processor 105 may apply an International Color Consortium (ICC) input colour profile for the scanner 115 to adjust the captured image data.

In step 1195, the processor 105 retrieves the optical dot gain property (i.e., light scattering property) of the selected print medium from memory 106 or the hard disk drive 110. The method 1100 concludes in step 1170, where the resolution of the printing device 160 is determined and corrected according to the retrieved optical dot gain, in accordance with the method 2000.

Figure 12:
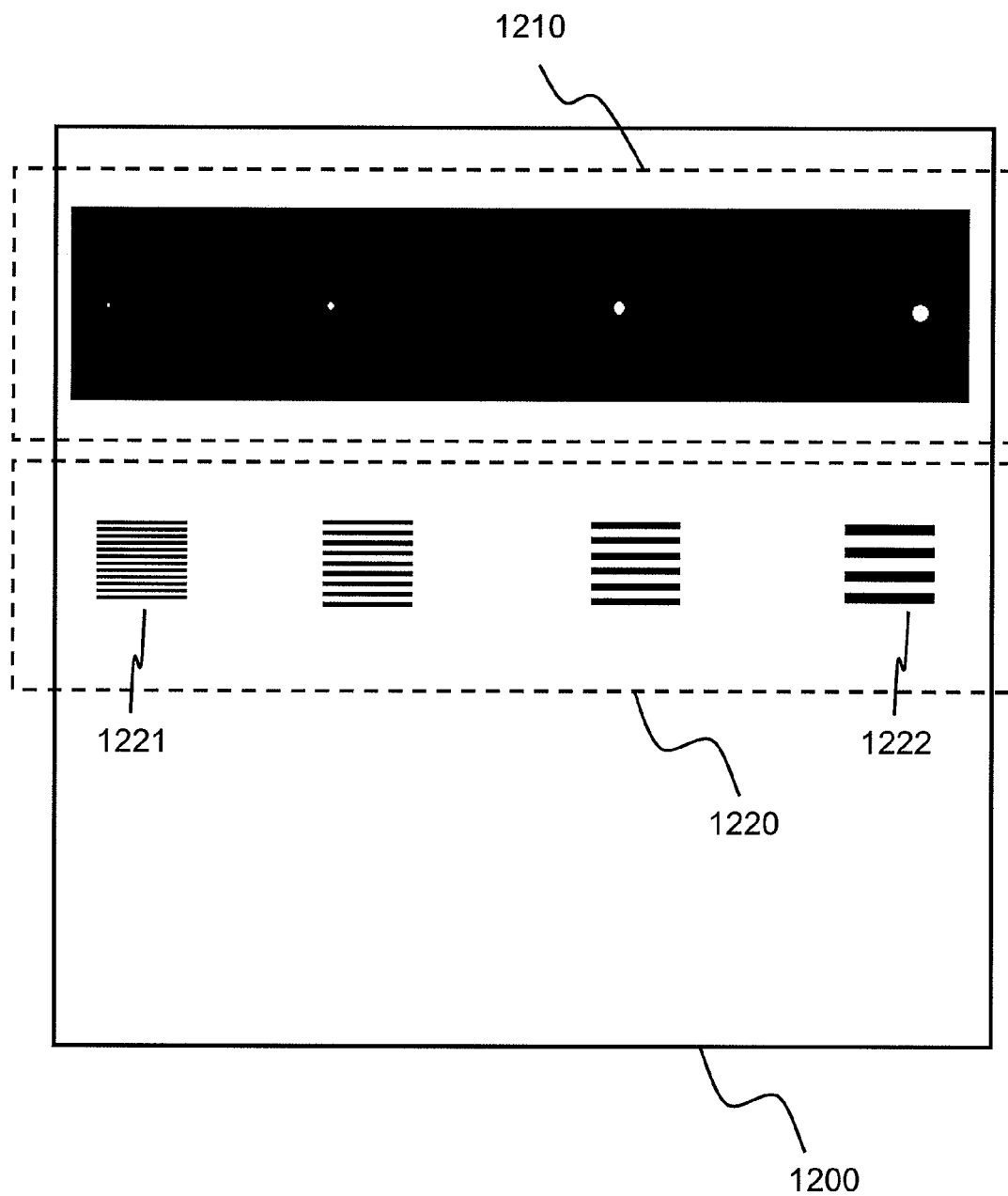
FIG. 12 shows a test chart.

The first test chart 1200 that is printed in step 1130 will now be described in more detail with respect to FIG. 12. FIG. 12 shows the first test chart 1200 for use in determining the resolution of the printer 160, where the optical dot gain property of the selected type of print medium is not known beforehand. Image data representing the first test chart 1200 may be stored as an image file in the memory 106 or the hard disk drive 110. The stored image data representing the first test chart may then be sent to the printer 160 for printing at step 1130. Alternately, the image data representing the test chart 1200 may be stored as firmware in a memory (not shown) of the printer 160 and be printed directly from the printer 160.

The test chart 1200 comprises two regions in the form of an optical scattering characterisation region 1210 and a contrast transfer characterisation region 1220.

The optical scattering characterisation region 1210 is a transmission mask similar to the transmission mask 155. The region 1210 comprises white circular holes with no absorptive material, allowing transmission of light through the region 1210, inside each of the circular holes. The holes form a pattern similar to the test pattern 155. The size of each of the circular holes is different. The layout of the optical scattering characterisation region 1210 of FIG. 12 is illustrative only. The optical scattering characterisation region 1210 preferably comprises fifteen (15) circular holes arranged in a line across the region 1210 as shown in FIG. 12. In one embodiment, the preferred diameters of the fifteen circular holes are: 0.085 mm, 0.169 mm, 0.254 mm, 0.339 mm, 0.423 mm, 0.508 mm, 0.593 mm, 0.677 mm, 0.762 mm, 0.850 mm, 0.931 mm, 1.016 mm, 1.101 mm, 1.185 mm and 1.270 mm. However, it was not possible to fully show the optical scattering characterisation region 1210 with the fifteen (15) circular due to the size of the holes. Accordingly, the optical scattering characterisation region 1210 is shown in FIG. 12 divided into three (3) holes.

In another embodiment, the optical scattering characterisation region 1210 may have the same form as the transmission mask 153 described above with sixteen (16) square regions each with an array of circular holes. The contrast transfer characterisation region 1220 comprises contrast transfer function (CTF) patterns in regions (e.g., 1221, 1222) that are similar to those of a USAF 1951 resolution target, but with a different number of bars at different spatial resolution. The regions (e.g., 1221, 1222) of the contrast transfer characterisation region 1220 form a test pattern in a similar manner to the test pattern 155 and the patches of transmission mask 500.

Again, the layout of the contrast transfer characterisation region 1220 of FIG. 12 is illustrative only. The contrast transfer characterisation region 1220 preferably comprises seven (7) regions (e.g., 1221, 1222) of CTF bars arranged across the region 1220 as shown in FIG. 12. The spatial frequencies of the CTF bars in each of the seven regions (e.g., 1221) are preferably of 300 line-pairs per inch (lpi), 150 lpi, 75 lpi, 37.5 lpi, 18.75 lpi, 9.375 lpi and 4.6875 lpi. For example, the spatial frequency of the CTF bars of the region 1221 is preferably 300 lpi and the spatial frequency of the CTF bars of the region 1222 is preferably 37.5 lpi. However, the CTF bars of the regions of the contrast transfer characterisation region 1220 may have various other spatial frequencies.

Figure 13:
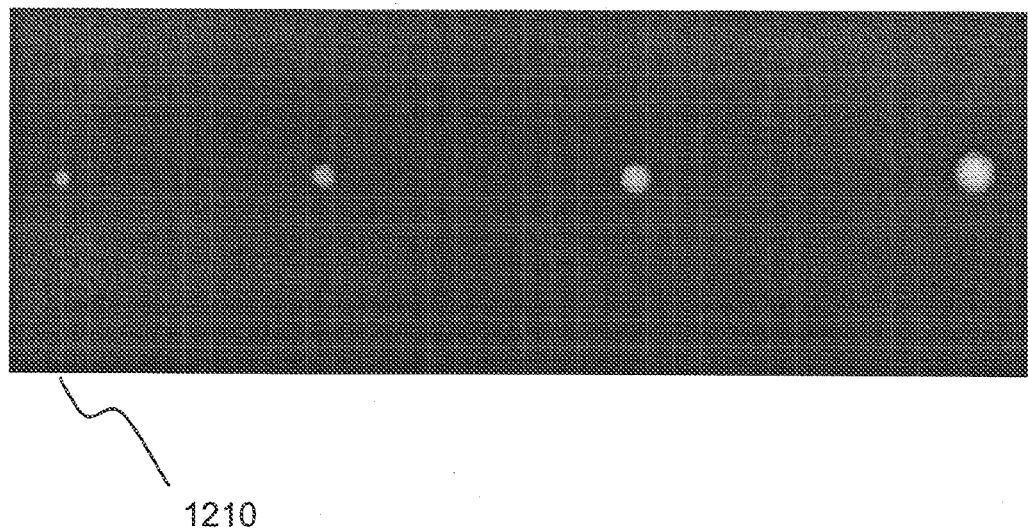
FIG. 13 shows a portion of a scan of an optical scattering characterisation region of the test chart of FIG. 12.

FIG. 13 shows a portion of a scan of the optical scattering characterisation region 1210 shown in FIG. 12.

Figure 14:
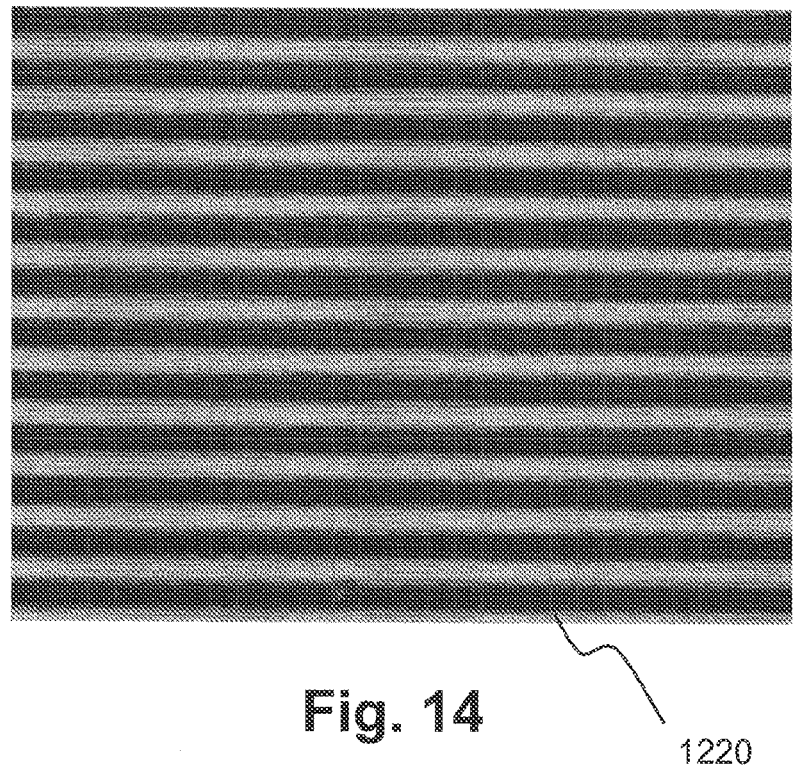
FIG. 14 shows a portion of a scan of a representative contrast transfer characterisation region the test chart of FIG. 12.

FIG. 14 shows a portion of a scan of the representative contrast transfer characterisation region 1220 shown in FIG. 12.

The step 1150 in which the light scattering property of the selected print medium is determined, will now be described below in more detail.

Figure 15:
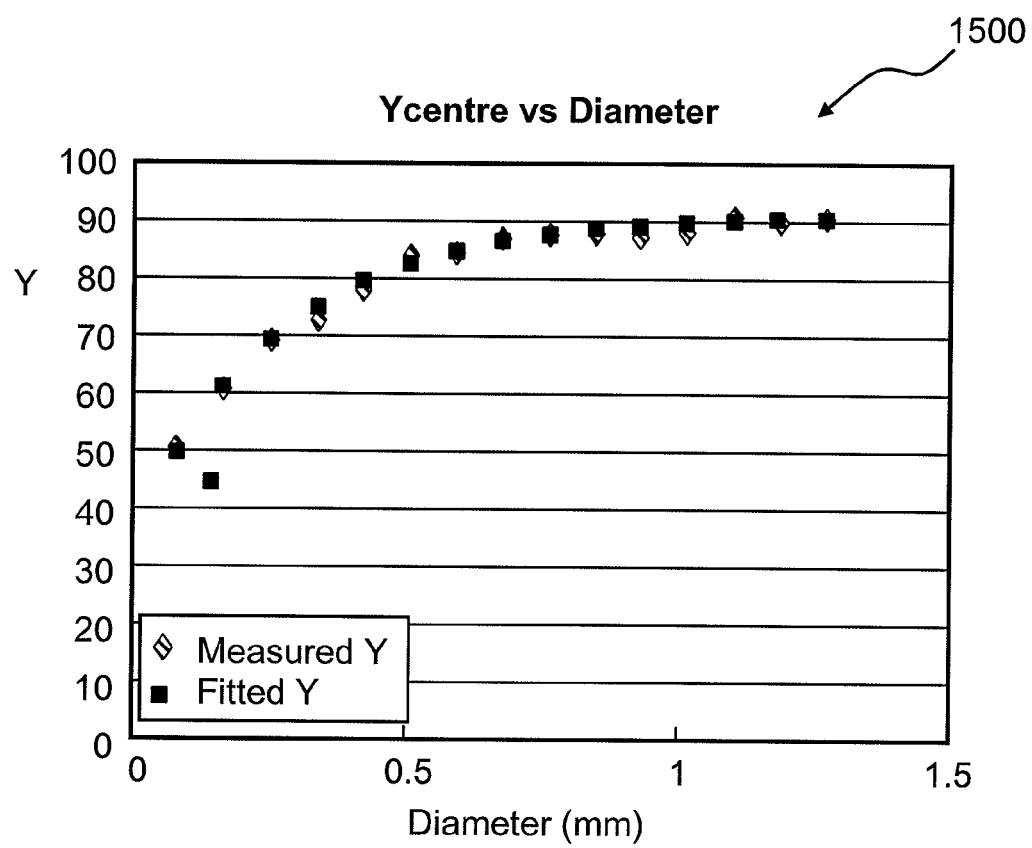
FIG. 15 shows a plot of luminance at the centre of white circular holes against diameters of the white circular.

In order to obtain the optical scattering property of the selected medium, at step 1150, luminance Y at a centre of each of the fifteen (15) circular holes, Ycentre, in the optical scattering characterisation region 1210 of FIG. 12, is measured. Accordingly, a luminance value, Ycentre, is determined for each of the fifteen (15) circular holes. The measured Ycentre values are fitted to a function in accordance with Equation (18) below:

$$Y\text{centre} = A - B\exp(-kr) \qquad (18)$$

where r is the radius in mm of a particular circular hole in the transmission mask of region 1210, and A, B and k are free parameters which characterise the optical scattering property of the selected print medium and hence the optical dot gain property of the print medium. FIG. 15 shows a plot 1500 of the measure luminance values, Ycentre, against the radius of each of the white circular holes of the optical scattering characterisation region 1210. The luminance value, Ycentre, changes with the diameter of the circular holes due to optical scattering.

As described above, in step 1170, the resolution of the printer 160 is determined and corrected according to either a retrieved or determined optical dot gain property of the print medium. It may observed that, for a printed CTF pattern formed by one of the regions (e.g., 1221) of the region 1220, the minimum average luminance value, Ymin, is not very sensitive to physical or optical dot gain. However, maximum average luminance value, Ymax, is sensitive to both optical dot gain and physical dot gain. The maximum average luminance value, Ymax, in the CTF pattern, instead of CTF itself, is used as an indicator of the resolution of the printer 160.

Figure 20:
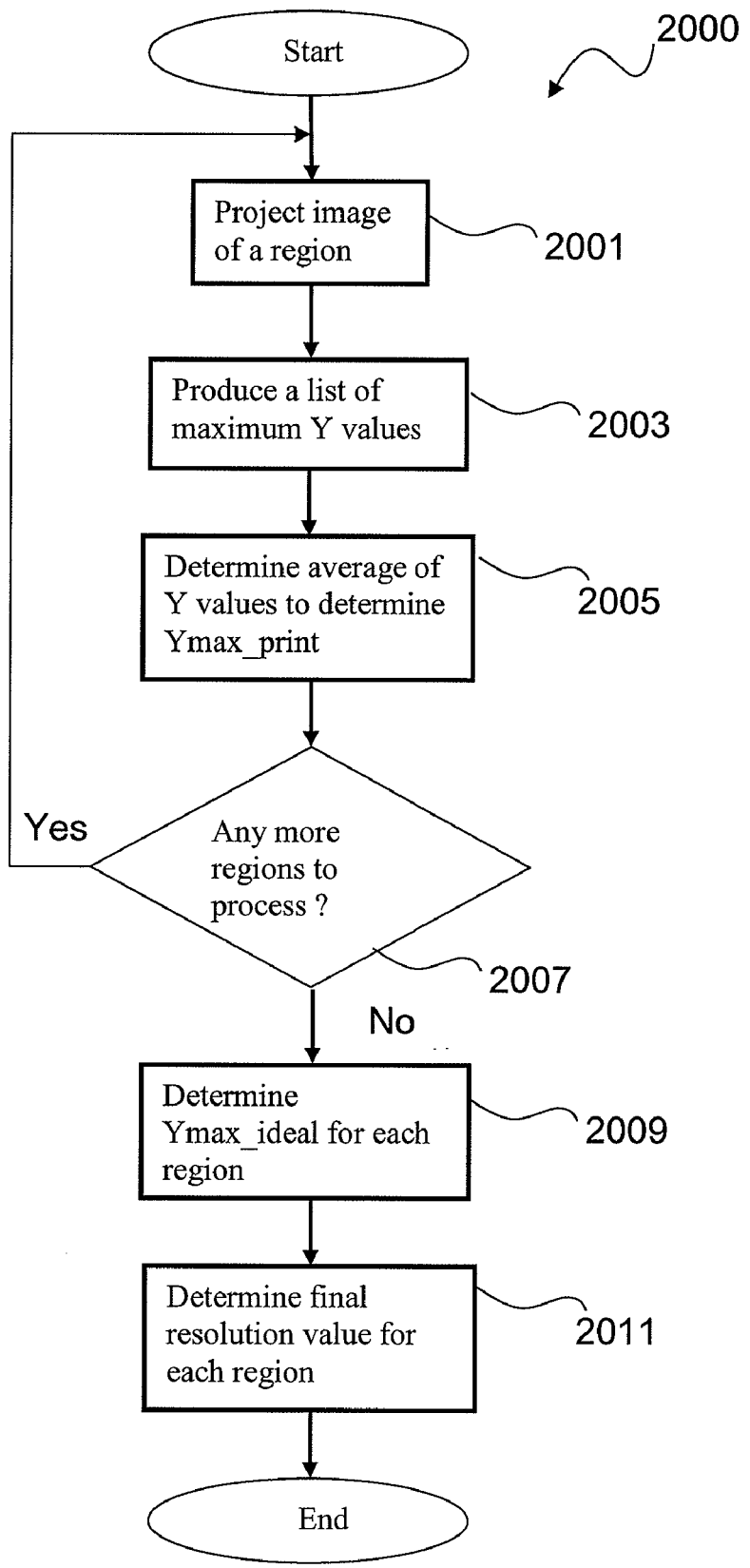
FIG. 20 is a flow diagram showing a method of determining the resolution of a printing device.

The method 2000 of determining the resolution of the printer 160, as executed at step 1170, will now be described with reference to FIG. 20. One or more of the steps of the method 2000 may be implemented as software resident on the hard disk drive 110 and being controlled in its execution by the processor 105.

The method 2000 begins at a first step 2001, where an image of a first region (e.g., 1221) of CTF bars of the contrast transfer characterisation region 1220 (i.e., a first CTF pattern) is projected along the black/white lines of the region 1221 to produce a one-dimensional signal.

Then at a next step 2003, a search along the one-dimensional signal is made to produce a list of maximum luminance values, Ymax, which may be stored in the memory 106. At a next step 2005, the processor 105 determines an average of the stored maximum luminance values, Ymax to determine a maximum print luminance value, Ymax_print, for the first region 1221.

At a next step 2007, if the processor 105 determines that there are more regions of CTF bars of the contrast transfer characterisation region 1220 to be processed, then the method 2000 returns to step 2001 to determine the Ymax_print value of a next region of the contrast transfer characterisation region 1220. Otherwise, the method 2000 proceeds to step 2009.

Figure 17:
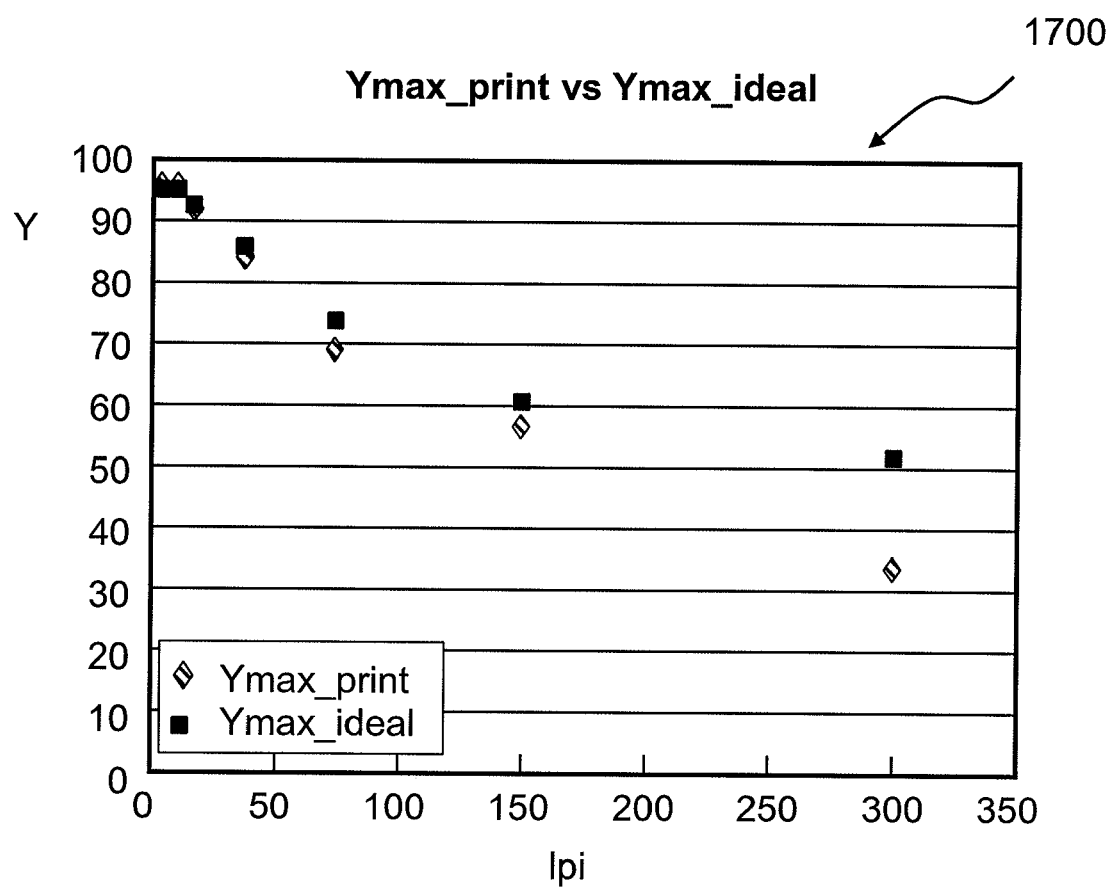
FIG. 17 shows a plot of measured maximum luminance values in CTF patterns and corresponding calculated maximum luminance values of an ideal printer at different spatial frequencies.

The measured maximum print luminance value, Ymax_print, of each of the regions (e.g., 1221) of the contrast transfer characterisation region 1220 decreases with the spatial frequencies of the CTF bars in each of the regions as can be seen in a plot 1700 of maximum print luminance value, Ymax_print, against spatial frequency as seen in FIG. 17. The decrease of measured maximum print luminance value, Ymax_print, is caused by a combined effect of physical dot gain and optical dot gain. Without these dot gains, the Ymax_print values will not change with the spatial frequencies of the CTF bars in each of the regions, and the contrast of each of the regions (i.e., the CTF patterns) of the contrast transfer characterisation region 1220 will always be one (1).

Figure 16:
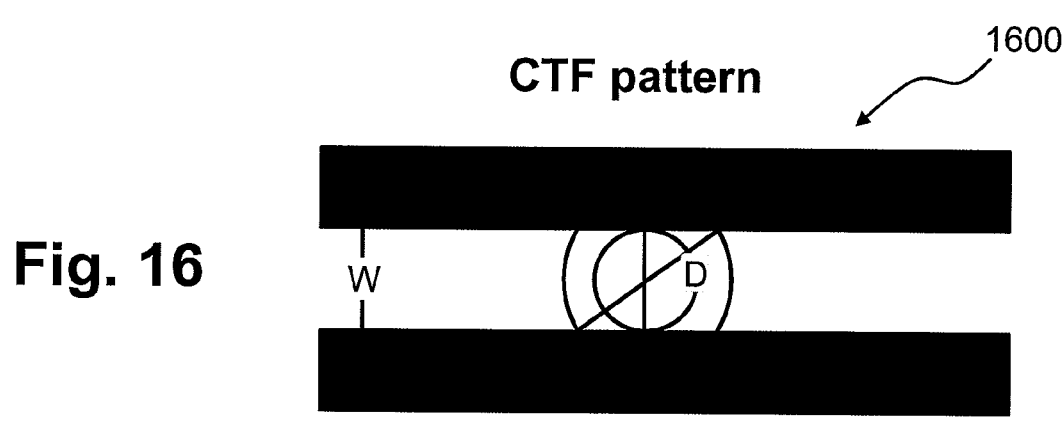
FIG. 16 shows a simplified geometric representation of a CTF pattern.

At step 2009, the processor 105 determines an ideal printer resolution value, Ymax_ideal, for each of the regions of the contrast transfer characterisation region 1220. Ymax_ideal is a luminance value that does not have any physical dot gain, and is therefore indicative of the resolution of the printer 160. FIG. 16 shows a simplified geometric representation of a CTF pattern 1600 on which ideal printer resolution value, Ymax_ideal, can be calculated at different spatial frequencies or line widths (W) in accordance with Equation (19) as follows:

$$Y\text{max\_ideal} = A - Be^{-kW} + \int_W^\infty \frac{2\sin^{-1}(W/D)}{\pi} Bke^{-kD} dD \quad (19)$$

The determined Ymax_ideal of the ideal printer together with the measured Ymax_print for the printer 160 at spatial frequencies of 300 lpi, 150 lpi, 75 lpi, 37.5 lpi, 18.75 lpi, 9.375 lpi and 4.6875 lpi are demonstrated in the plot 1700 of FIG. 17.

Figure 19:
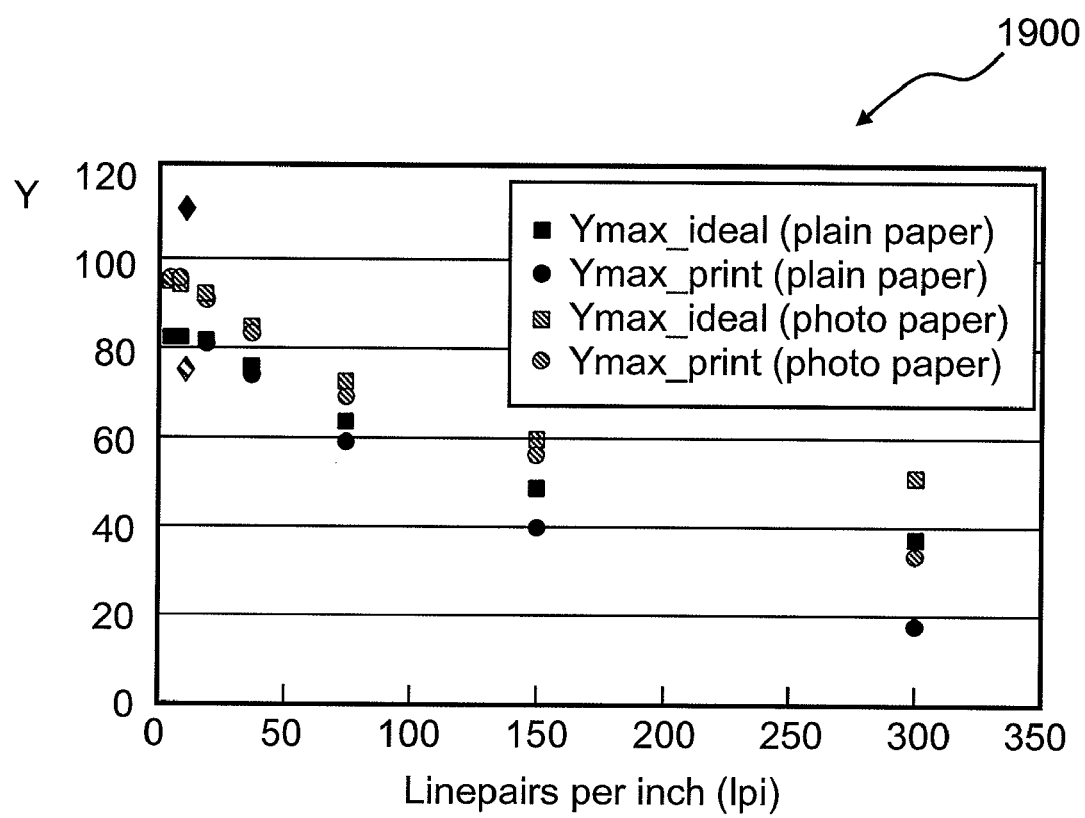
FIG. 19 shows a plot of resolution metrics versus spatial frequency measured from two different papers.

The method 2000 concludes at a next step 2011, where a final resolution value for the printer 160 is determined for each of the regions of the contrast transfer characterisation region 1220 as the difference of Ymax_ideal and Ymax_print for that region. Since the final resolution value has been compensated for optical scattering of the print medium (or paper) being used, the final resolution value should be largely a metric independent of light scattering property of the print medium (e.g., paper) used. As can be seen in FIG. 19, there are substantially no differences between distances between the Ymax_ideal and Ymax_print values for plain paper and Ymax_ideal and Ymax_print values for photo paper.

Figure 18:
FIG. 18 shows another test chart.

FIG. 18 shows an example of the test chart 1800 (or transmission mask) as printed at step 1180 for use in determining the resolution of the printer 160 where the optical property is previously known. The test chart 1800 is the same as the contrast transfer characterisation region 1220.

Any of the variations of the embodiments described above may be used to determine the optical scattering property of the print medium.

INDUSTRIAL APPLICABILITY

It is apparent from the above that the arrangements described are applicable to the computer and data processing industries.

The foregoing describes only some embodiments of the present invention, and modifications and/or changes can be made thereto without departing from the scope and spirit of the invention, the embodiments being illustrative and not restrictive. For example, the imaging device described above was the scanner 115. Any other suitable imaging device such as a drum scanner, a microscope, a still camera or video camera may also be used to capture the image at steps 320 and 1020. Further, for the method 1000 described above, an array of photo-sensors may be used instead of an imaging device, as only the mean reflectance of each region is determined. In this instance, the reflected illumination may be measured using a photo-sensor for each of the regions of the test pattern 510. Accordingly, the illumination reflected from the medium may be measured using a two dimensional array of sensors.

In one embodiment, the patterns of the transmission masks 153 and 500 may be projected onto a medium and then an image of the projected pattern may be captured.

Furthermore, in one embodiment, the transmission mask 153 pattern may be printed onto the medium 152, thereby producing a chart in which the ink on the medium forms the transmission mask.

For the transmission mask 153 and the region 1222, circular holes were used as the pattern. For certain sorts of media, there may be anisotropic light scattering, due to a preferred orientation for cellulose fibres in a matrix of the medium (e.g., paper matrix). The anisotropic light scattering effect may be determined by using ellipses as the pattern in the transmission mask 153 or the region 1222. In this instance, each square region of the transmission mask 153 defines a pattern comprising ellipses. The difference in the central intensity in the ellipses of different orientations may be used to determine angular dependence of the scattering function.

The embodiments described above were based on a flat bed scanner 115 connected to a host computer module 101. A variety of other systems may be configured with the same functionality. In particular, the computer system 100 may be an embedded system, and the imaging system may also be embedded in another device. For example, the computing system 100 may comprise a printing system. In this instance, before a medium is printed using the printing system, the light scattering properties of the medium may be determined by placing the medium in contact with a transmission mask. A corresponding printing process may then be modified to adjust what is printed based on the determined light scattering properties of the medium that it is being printed on. The described methods may also be executed by a printing device of such a printing system.

In the context of this specification, the word "comprising" means "including principally but not necessarily solely" or "having" or "including", and not "consisting only of". Variations of the word "comprising", such as "comprise" and "comprises" have correspondingly varied meanings.

The invention claimed is:

1. A method of determining a light scattering property of a medium, said method comprising the steps of
   illuminating the medium through a test pattern, the test pattern comprising at least one region containing a first pattern with substantial variation in two orthogonal directions at one scale, the test pattern further comprising at least one other region containing the first pattern at a different scale, wherein a density of the at least one region is substantially the same as a density of the at least one other region;
   measuring light reflected from the illuminated medium through the test pattern; and
   determining a light scattering property of the medium based on the measured light.

2. A method according to claim 1, wherein the light scattering property of the medium is determined based on a difference between the measure light in each of the at least one region and the at least one other region.

3. The method according to claim 1, wherein the pattern comprises circles.

4. The method according to claim 1, wherein the pattern comprises ellipses.

5. The method according to claim 1, wherein the test pattern further comprises at least another region containing a second pattern at one scale, and at least one other region containing the second pattern at a different scale.

6. The method according to claim 5, wherein the first and second pattern have substantially equal mean transmittance.

7. The method according to claim 1, wherein the reflected light is measured using a two dimensional array of sensors.

8. The method according to claim 1, wherein the reflected light is measured using a one dimensional sensor scanned across the test pattern.

9. The method according to claim 1, wherein the reflected light is measured using a photo-sensor for each of the regions of the test pattern.

10. The method according to claim 1, wherein the method is executed by a printing device.

11. The method according to claim 1, wherein the test pattern is produced on a glass substrate that is placed in contact with the medium.

12. An apparatus for determining a light scattering property of a medium, said apparatus comprising:
    illuminating device for illuminating the medium through a test pattern, the test pattern comprising at least one region containing a first pattern with substantial variation in two orthogonal directions at one scale, the test pattern further comprising at least one other region containing the first pattern at a different scale, wherein a density of the at least one region is substantially the same as a density of the at least one other region;
    imaging device for measuring light reflected from the illuminated medium through the test pattern to capture an image of the illuminated medium; and
    processor for determining a light scattering property of the medium based on the measured light.

13. A computer readable medium, having a program recorded on the medium, where the program is configured to make a computer execute a process to determine a light scattering property of a medium, said program comprising:
    code for illuminating the medium through a test pattern, the test pattern comprising at least one region containing a first pattern with substantial variation in two orthogonal directions at one scale, the test pattern further comprising at least one other region containing the first pattern at a different scale, wherein a density of the at least one region is substantially the same as a density of the at least one other region;
    code for measuring the light reflected from the illuminated medium through the test pattern to capture an image of the illuminated medium; and
    code for determining a light scattering property of the medium based on the measured light.

14. A method of determining a resolution measurement for a printer based on a medium on which the printer prints, said method comprising the steps of
    illuminating an area of the medium through a test pattern, the test pattern comprising at least one region containing a first pattern with substantial variation in two orthogonal directions at one scale, the test pattern further comprising at least one other region containing the first pattern at a different scale;
    measuring light reflected from the illuminated area of the medium through the test pattern;
    determining a light scattering property of the area of the medium based on the measured light;
    printing a second test pattern for determining printer resolution, on a second area of said medium;
    determining resolution of said printer based on an image of said second test pattern; and
    correcting the determined resolution for said printer based on said light scattering property.

15. The method according to claim 14, wherein the first test pattern comprises circles.

16. The method according to claim 14, wherein the first test pattern comprises ellipses.

17. The method according to claim 14, wherein the reflected light is measured using a two dimensional array of sensors.

18. The method according to claim 14, wherein the reflected light is measured using a one dimensional sensor scanned across the test pattern.

19. The method according to claim 14, wherein the reflected light is measured using a photo-sensor for each of the regions of the test pattern.

20. The method according to claim 14, wherein the test pattern is produced on a glass substrate that is placed in contact with the medium.

21. An apparatus for determining a resolution measurement for a printer based on a medium on which the printer prints, said apparatus comprising:
    means for illuminating an area of the medium through a test pattern, the test pattern comprising at least one region containing a first pattern with substantial variation in two orthogonal directions at one scale, the test pattern further comprising at least one other region containing the first pattern at a different scale;
    means for measuring light reflected from the illuminated area of the medium through the test pattern;
    means for determining a light scattering property of the area of the medium based on the measured light;
    means for printing a second test pattern for determining printer resolution, on a second area of said medium;
    means for determining resolution of said printer based on an image of said second test pattern; and
    means for correcting the determined resolution for said printer based on said light scattering property.

22. A computer readable medium, having a program recorded on the medium, where the program is configured to make a computer execute a process to determine a light scattering property of a medium, said program comprising:
    code for determining a resolution measurement for a printer based on a medium on which the printer prints, said method comprising the steps of
    code for illuminating an area of the medium through a test pattern, the test pattern comprising at least one region containing a first pattern with substantial variation in two orthogonal directions at one scale, the test pattern further comprising at least one other region containing the first pattern at a different scale;
    code for measuring light reflected from the illuminated area of the medium through the test pattern;
    code for determining a light scattering property of the area of the medium based on the measured light;
    code for printing a second test pattern for determining printer resolution on a second area of said medium;
    code for determining resolution of said printer based on an image of said second test pattern; and
    code for correcting the determined resolution for said printer based on said light scattering property.

* * * * *